United States Patent
Kim et al.

(10) Patent No.: US 9,051,328 B2
(45) Date of Patent: Jun. 9, 2015

(54) HETEROCYCLIC COMPOUND AND ORGANIC LIGHT-EMITTING DEVICE INCLUDING THE SAME

(75) Inventors: Young-Kook Kim, Yongin (KR); Seok-Hwan Hwang, Yongin (KR); Yoon-Hyun Kwak, Yongin (KR); Hye-Jin Jung, Yongin (KR); Jong-Hyuk Lee, Yongin (KR); Jin-O Lim, Yongin (KR); Hee-Joo Ko, Yongin (KR)

(73) Assignee: Samsung Display Co., Ltd., Yongin-si (KR)

(*) Notice: Subject to any disclaimer, the term of this patent is extended or adjusted under 35 U.S.C. 154(b) by 264 days.

(21) Appl. No.: 12/858,130

(22) Filed: Aug. 17, 2010

(65) Prior Publication Data
US 2011/0049488 A1 Mar. 3, 2011

(30) Foreign Application Priority Data
Sep. 3, 2009 (KR) ........................ 10-2009-0083155

(51) Int. Cl.
| | |
|---|---|
| H01L 51/54 | (2006.01) |
| C07D 487/04 | (2006.01) |
| C07D 401/14 | (2006.01) |
| C07D 487/06 | (2006.01) |
| C09K 11/06 | (2006.01) |
| H05B 33/14 | (2006.01) |
| H01L 51/00 | (2006.01) |
| H01L 51/50 | (2006.01) |

(52) U.S. Cl.
CPC .............. *C07D 487/06* (2013.01); *C09K 11/06* (2013.01); *C09K 2211/1007* (2013.01); *C09K 2211/1011* (2013.01); *C09K 2211/1029* (2013.01); *C09K 2211/1044* (2013.01); *H01L 51/0058* (2013.01); *H01L 51/0061* (2013.01); *H01L 51/0067* (2013.01); *H01L 51/0072* (2013.01); *H01L 51/5016* (2013.01); *H01L 51/5048* (2013.01); *H01L 51/5092* (2013.01); *H05B 33/14* (2013.01)

(58) Field of Classification Search
None
See application file for complete search history.

(56) References Cited

U.S. PATENT DOCUMENTS

| | | | |
|---|---|---|---|
| 6,465,115 B2 | 10/2002 | Shi et al. | |
| 6,596,415 B2 | 7/2003 | Shi et al. | |
| 7,051,949 B2 | 5/2006 | Aiyama | |
| 7,700,201 B2 | 4/2010 | Seo et al. | |

(Continued)

FOREIGN PATENT DOCUMENTS

| | | |
|---|---|---|
| CN | 101080478 A | 11/2007 |
| JP | 2008078362 A | 4/2008 |

(Continued)

OTHER PUBLICATIONS

Registration Determination Certificate issued by the Korean Intellectual Property Offie for Korean Application No. 10-2009-0083155 on Nov. 30, 2011.

(Continued)

*Primary Examiner* — J. L. Yang
(74) *Attorney, Agent, or Firm* — Christie, Parker & Hale, LLP

(57) ABSTRACT

Embodiments of the present invention are directed to heterocyclic compounds and organic light-emitting devices including the heterocyclic compounds. The organic light-emitting devices using the heterocyclic compounds have high-efficiency, low driving voltages, high luminance and long lifespans.

18 Claims, 1 Drawing Sheet

(56) References Cited

U.S. PATENT DOCUMENTS

| | | |
|---|---|---|
| 7,714,323 B2 | 5/2010 | Hwang et al. |
| 7,745,819 B2 | 6/2010 | Lee et al. |
| 7,901,794 B2 | 3/2011 | Sugimoto et al. |
| 2007/0069203 A1* | 3/2007 | Lee et al. ............ 257/40 |
| 2007/0176163 A1 | 8/2007 | Drolet et al. |
| 2008/0203905 A1 | 8/2008 | Je et al. |
| 2009/0033212 A1* | 2/2009 | Ahn et al. ............ 313/504 |
| 2009/0159877 A1 | 6/2009 | Meng |
| 2010/0155714 A1 | 6/2010 | Seo et al. |

FOREIGN PATENT DOCUMENTS

| | | |
|---|---|---|
| KR | 1020040057862 A | 7/2004 |
| KR | 20050107809 A | 11/2005 |
| KR | 1020070003586 A | 1/2007 |
| WO | WO 2006/090772 A1 | 8/2006 |
| WO | WO 2007/004799 A1 | 1/2007 |

OTHER PUBLICATIONS

European Search Report dated Dec. 23, 2010, for corresponding European Patent application 10251546.7.

Chinese Office action dated Dec. 26, 2013, for corresponding Chinese Patent application 201010272180.0, (7 pages).

SIPO Certificate of Final Registration Determination, dated Mar. 25, 2015, for corresponding Chinese Patent application 201010272180.0, (35 pages).

* cited by examiner

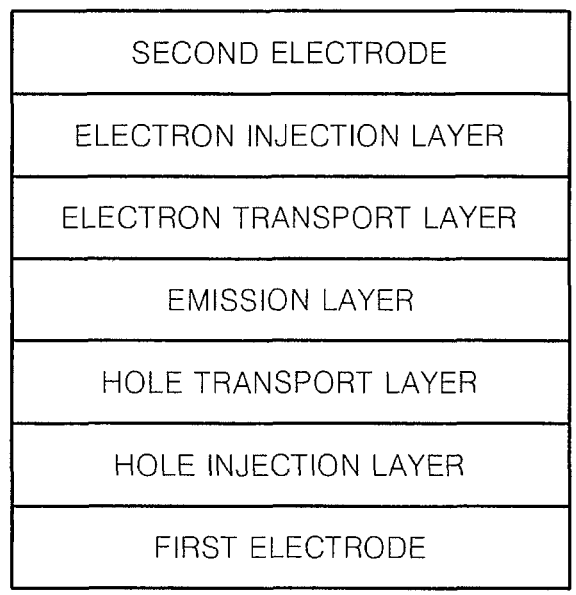

HETEROCYCLIC COMPOUND AND ORGANIC LIGHT-EMITTING DEVICE INCLUDING THE SAME

CROSS-REFERENCE TO RELATED PATENT APPLICATION

This application claims priority to and the benefit of Korean Patent Application No. 10-2009-0083155, filed on Sep. 3, 2009, in the Korean Intellectual Property Office, the entire content of which is incorporated herein by reference.

BACKGROUND OF THE INVENTION

1. Field of the Invention

The present invention relates to heterocyclic compounds and organic light-emitting devices including the heterocyclic compounds.

2. Description of the Related Art

Organic light-emitting devices are self-emission type display devices, and have wide viewing angles, high contrast ratios, and short response times. Due to these characteristics, organic light-emitting devices are drawing much attention.

Light-emitting devices can be categorized into inorganic light-emitting devices which include emission layers containing inorganic compounds, and organic light-emitting devices which include containing organic compounds. Research has been actively conducted into organic light-emitting devices, since organic light-emitting devices have higher luminance, lower driving voltages, and shorter response times than inorganic light-emitting devices, and organic light-emitting devices can produce more colors than inorganic light emitting devices.

Typically, an organic light-emitting device has a stack structure including an anode, a cathode and an organic emission layer therebetween. However, a hole injection layer and/or a hole transport layer may be further stacked between the anode and the organic emission layer, and/or an electron transport layer may be further stacked between the organic emission layer and the cathode. In other words, an organic light-emitting device may have an anode/hole transport layer/organic emission layer/cathode stack structure, or an anode/hole transport layer/organic emission layer/electron transport layer/cathode stack structure.

Organic light-emitting devices including known light-emitting materials do not have satisfactory life span, luminescence efficiency, or power consumption characteristics, thus leaving much room for improvement.

SUMMARY OF THE INVENTION

According to embodiments of the present invention, an organic layer material has improved electrical stability and charge transport capabilities, high glass transition temperature, and improved ability to prevent crystallization. The organic layer material is suitable for fluorescent or phosphorescent organic light-emitting devices (OLEDs) which can realize all colors, including red, green, blue, and white.

In some embodiments of the present invention, a method of preparing the organic layer material is provided.

In other embodiments of the present invention, an organic light-emitting device includes an organic layer including the organic layer material.

In yet other embodiments of the present invention, a flat panel display device includes the organic light-emitting device.

According to embodiments of the present invention, a heterocyclic compound includes a compound represented by Formula 1 below:

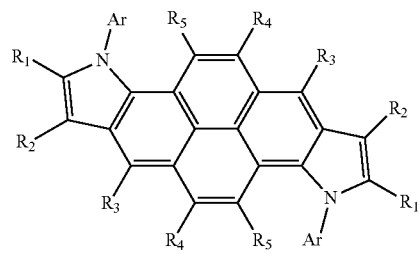

Formula 1

In Formula 1, Ar may be selected from substituted and unsubstituted $C_6$-$C_{60}$ aryl groups, substituted and unsubstituted $C_4$-$C_{60}$ heteroaryl groups, amino groups substituted with at least one substituted or unsubstituted $C_6$-$C_{50}$ aryl group, and substituted and unsubstituted $C_6$-$C_{60}$ condensed polycyclic groups. Each of $R_1$ through $R_5$ is independently selected from hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_6$-$C_{50}$ aryloxy groups, substituted and unsubstituted $C_6$-$C_{50}$ arylthio groups, amino groups substituted with at least one substituted or unsubstituted $C_6$-$C_{50}$ aryl group, substituted and unsubstituted $C_3$-$C_{50}$ carbocyclic groups, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups. In some embodiments, two or more adjacent R groups selected from $R_1$, $R_2$, $R_3$, $R_4$ and $R_5$ may form an aromatic ring.

According to other embodiments of the present invention, an organic light-emitting device includes a first electrode, a second electrode, and an organic layer between the first electrode and the second electrode. The organic layer includes at least one organic layer including the heterocyclic compound.

According to other embodiments of the present invention, an organic light-emitting device includes a first electrode, a second electrode, and an organic layer between the first electrode and the second electrode. The organic layer includes at least one layer comprising the heterocyclic compound, which layer can be formed using a wet process.

The at least one layer of the organic layer may be formed using a wet process.

BRIEF DESCRIPTION OF THE DRAWING

The above and other features and advantages of the present invention will become more apparent by reference to the following detailed description when considered in conjunction with the attached drawing in which:

FIG. 1 is a schematic diagram depicting the structure of an organic light-emitting device according to an embodiment of the present invention.

DETAILED DESCRIPTION OF THE INVENTION

According to some embodiments of the present invention, a heterocyclic compound is represented by Formula 1 below, and the heterocyclic compound may be used to form an organic layer of an organic light-emitting device (OLED).

Formula 1

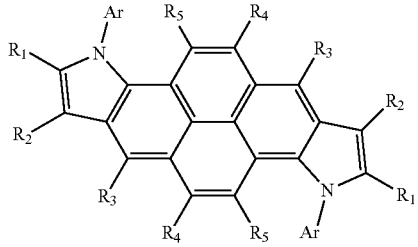

In Formula 1, Ar may be selected from substituted and unsubstituted $C_6$-$C_{60}$ aryl groups, substituted and unsubstituted $C_4$-$C_{60}$ heteroaryl groups, amino groups substituted with at least one substituted or unsubstituted $C_6$-$C_{50}$ aryl group, and substituted and unsubstituted $C_6$-$C_{60}$ condensed polycyclic groups. Each of $R_1$ through $R_5$ may be independently selected from hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_6$-$C_{50}$ aryloxy groups, substituted and unsubstituted $C_6$-$C_{50}$ arylthio groups, amino groups substituted with at least one substituted or unsubstituted $C_6$-$C_{50}$ aryl group, substituted and unsubstituted $C_3$-$C_{50}$ carbocyclic groups, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups. In some embodiments, at least two adjacent R groups selected from $R_1$, $R_2$, $R_3$, $R_4$ and $R_5$ may form an aromatic ring.

For example, in Formula 1, Ar may be selected from substituted and unsubstituted aryl groups having from 6 to 60 ring carbon atoms (for example, from 6 to 18 ring carbon atoms), and substituted and unsubstituted heteroaryl groups having from 4 to 60 ring carbon atoms (for example, from 5 to 20 ring carbon atoms).

Nonlimiting examples of the aryl group represented by Ar include phenyl groups, 1-naphthyl groups, 2-naphthyl groups, 1-anthracenyl groups, 2-anthracenyl groups, 9-anthracenyl groups, 1-phenanthryl groups, 2-phenanthryl groups, 3-phenanthryl groups, 4-phenanthryl groups, 9-phenanthryl groups, 1-naphthacenyl groups, 2-naphthacenyl groups, 9-naphthacenyl groups, 1-pyrenyl groups, 2-pyrenyl groups, 4-pyrenyl groups, 2-biphenylyl groups, 3-biphenylyl groups, 4-biphenylyl groups, p-terphenyl-4-yl groups, p-terphenyl-3-yl groups, p-terphenyl-2-yl groups, m-terphenyl-4-yl groups, m-terphenyl-3-yl groups, and m-terphenyl-2-yl groups.

Nonlimiting examples of the heteroaryl group represented by Ar include thiophenyl groups, 1-phenylthiophenyl groups, 1,4-diphenylthiophenyl groups, benzothiophenyl groups, 1-phenylbenzothiophenyl groups, 1,8-diphenylbenzothiophenyl groups, furyl groups, 1-phenyldibenzothiophenyl groups, 1,8-diphenylthiophenyl groups, dibenzofuranyl groups, 1-phenyldibenzofuranyl groups, 1,8-diphenyldibenzofuranyl groups, and benzothiazolyl groups.

Nonlimiting examples of the aryloxy group represented by $R_1$ through $R_5$ include phenyloxy groups, 1-naphthyloxy groups, 2-naphthyloxy groups, 4-biphenylyloxy groups, p-terphenyl-4-yloxy groups, and p-tolyloxy groups. For example, the aryloxy group may be a phenyloxy group or a 2-naphthyloxy group.

Nonlimiting examples of the arylthio group represented by $R_1$ through $R_5$ include phenylthio groups, 1-naphthylthio groups, 2-naphthylthio groups, 4-biphenylylthio groups, p-terphenyl-4-ylthio groups, and p-tolylthio groups. For example, the arylthio group may be a phenylthio group or a 2-naphthylthio group.

Nonlimiting examples of the alkoxycarbonyl group represented by $R_1$ through $R_5$ include methoxycarbonyl groups, ethoxycarbonyl groups, n-propoxycarbonyl groups, iso-propoxycarbonyl groups, n-butoxycarbonyl groups, and tert-butoxycarbonyl groups. For example, the alkoxycarbonyl group may be a methoxycarbonyl group or an ethoxycarbonyl group.

In the amino group (represented by $R_1$ through $R_5$) substituted with at least one substituted or unsubstituted $C_6$-$C_{50}$ aryl group, nonlimiting examples of the aryl group include those discussed above with respect to the aryl group represented by Ar.

In Formula 1 above, nonlimiting examples of the halogen atom include fluorine atoms, chlorine atoms, bromine atoms, and iodine atoms.

In some embodiments, for example, each of R1 and R2 may be independently selected from methyl groups, and substituted and unsubstituted monocyclic to tricyclic aryl groups. Nonlimiting examples of suitable unsubstituted monocyclic to tricyclic aryl or heteroayl groups include phenyl groups, naphthyl groups, biphenyl groups, terphenyl groups, fluorenyl groups, and carbazolyl groups. Nonlimiting examples of suitable substituted monocyclic to tricyclic aryl or heteroaryl groups include groups substituted with one to three substituents selected from C1-C5 alkyl groups, C1-C5 alkoxy groups, cyano groups, C1-C5 alkyl phenoxy groups, phenyl groups, halogen atoms, and —N(R')(R") groups wherein each of R' and R" is independently selected from the group consisting of hydrogen atoms, C1-C20 alkyl groups, C6-C20 aryl groups, and C3-C20 heteroaryl groups.

Each of the groups described above may be further substituted, and in some embodiments, may include at least two substituents which may be the same or different. The at least two substituents may be interconnected to form a ring.

Nonlimiting examples of the substituents for Ar and $R_1$ through $R_5$ include alkyl groups, alkenyl groups, alkynyl groups, amino groups, alkoxy groups, aryloxy groups, acyl groups, alkoxycarbonyl groups, aryloxycarbonyl groups, acyloxy groups, acylamino groups, alkoxycarbonylamino groups, aryloxycarbonylamino groups, sulfonylamino groups, sulfamoyl groups, carbamoyl groups, alkylthio groups, arylthio groups, sulfonyl groups, sulfinyl groups, ureide groups, phosphoricamide groups, hydroxyl groups, mercapto groups, halogen atoms, cyano groups, sulfo groups, carboxyl groups, nitro groups, hydroxamic acid groups, sulfino groups, hydrazino groups, imino groups, heterocyclic groups, and silyl groups. These substituents may be further substituted. In some embodiments, for example, Ar and $R_1$ through $R_5$ may each include at least two substituents which may be the same or different. The at least two substituents may be interconnected to form a ring.

Nonlimiting examples of the alkyl group include C1-C20 alkyl groups. In some embodiments for example, the alkyl group is selected from C1-C12 alkyl groups. In other embodiments, the alkyl group is selected from C1-C8 alkyl groups. Nonlimiting examples of suitable alkyl groups include methyl groups, ethyl groups, iso-propyl groups, tert-butyl groups, n-octyl groups, n-decyl groups, n-hexadecyl groups, cyclopropyl groups, cyclopentyl groups, and cyclohexyl groups.

Nonlimiting examples of the alkenyl group include C2-C20 alkenyl groups. In some embodiments, for example, the alkenyl group is selected from C2-C12 alkenyl groups. In other embodiments, the alkenyl group is selected from C2-C8 alkenyl groups. Nonlimiting examples of the alkenyl group include vinyl groups, allyl groups, 2-butenyl groups, and 3-pentenyl groups.

Nonlimiting examples of the alkynyl group include C2-C20 alkynyl group. In some embodiments, for example, the alkynyl group is a C2-C12 alkynyl group. In other embodiment, the alkynyl group is selected from C2-C8 alkynyl groups. A nonlimiting example of the alkynyl group is a 3-pentynyl group.

Nonlimiting examples of the amino group include C2-C20 amino groups. In some embodiments, for example, the amino group is a C2-C12 amino group. In other embodiments, the amino group is selected from C2-C6 amino groups. Nonlimiting examples of the amino group include amino groups, methylamino groups, dimethylamino groups, diethylamino groups, diphenylamino groups, and dibenzylamino groups.

Nonlimiting examples of the alkoxy group include C1-C20 alkoxy groups. In some embodiments, for example, the alkoxy group is a C1-C12 alkoxy group. In other embodiments, the alkoxy group is selected from C1-C8 alkoxy groups. Nonlimiting examples of the alkoxy group include methoxy groups, ethoxy groups, and butoxy groups.

Nonlimiting examples of the aryloxy group include C6-C20 aryloxy groups. In some embodiments, for example, the aryloxy group is a C6-C16 aryloxy group. In other embodiments, the aryloxy group is selected from C6-C12 aryloxy groups. Nonlimiting examples of the aryloxy group include phenyloxy groups, and 2-naphthyloxy groups.

Nonlimiting examples of the acyl group include C1-C20 acyl groups. In some embodiments, for example, the acyl group is a C1-C16 acyl group. In other embodiments, the acyl group is selected from C1-C12 acyl groups. Nonlimiting examples of the acyl group include acetyl groups, benzoyl groups, formyl groups, and pivaloyl groups.

Nonlimiting examples of the alkoxycarbonyl group include C2-C20 alkoxycarbonyl groups. In some embodiments, for example, the alkoxycarbonyl group is a C2-C16 alkoxycarbonyl group. In other embodiments, the alkoxycarbonyl group is selected from C2-C12 alkoxycarbonyl groups. Nonlimiting examples of the alkoxycarbonyl group include methoxycarbonyl groups, and ethoxycarbonyl groups.

Nonlimiting examples of the aryloxycarbonyl group include C7-C20 aryloxycarbonyl groups. In some embodiments, for example, the aryloxycarbonyl group is a C7-C16 aryloxycarbonyl group. In other embodiments, the aryloxycarbonyl group is selected from C7-C10 aryloxycarbonyl groups. A nonlimiting example of the aryloxycarbonyl group is a phenyloxycarbonyl group.

Nonlimiting examples of the acyloxy group include C2-C20 acyloxy groups. In some embodiments, for example, the acyloxy group is a C2-C16 acyloxy group. In other embodiments, the acyloxy group is selected from C2-C10 acyloxy groups. Nonlimiting examples of the acyloxy group include acetoxy groups and benzoyloxy groups.

Nonlimiting examples of the acylamino group include C2-C20 acylamino groups. In some embodiments, for example, the acylamino group is a C2-C16 acylamino group. In other embodiments, the acylamino group is selected from C2-C10 acylamino groups. Nonlimiting examples of the acylamino group include acetylamino groups, and benzoylamino groups.

Nonlimiting examples of the alkoxycarbonylamino group include C2-C20 alkoxycarbonylamino groups. In some embodiments, for example, the alkoxycarbonylamino group is a C2-C16 alkoxycarbonylamino group. In other embodiments, the alkoxycarbonylamino group is selected from C2-C12 alkoxycarbonylamino groups. A nonlimiting example of a alkoxycarbonylamino group is a methoxycarbonylamino group.

Nonlimiting examples of the aryloxycarbonylamino group include C7-C20 aryloxycarbonylamino groups. In some embodiments, for example, the aryloxycarbonylamino group is a C7-C16 aryloxycarbonylamino group. In other embodiments, the aryloxycarbonylamino group is selected from C7-C12 aryloxycarbonylamino groups. One nonlimiting example of an aryloxycarbonylamino group is a phenyloxycarbonylamino group.

Nonlimiting examples of the sulfonylamino group include C1-C20 sulfonylamino groups. In some embodiments, for example, the sulfonylamino group is a C1-C16 sulfonylamino group. In other embodiments, the sulfonylamino group is selected from C1-C12 sulfonylamino groups. Nonlimiting examples of the sulfonylamino group include methanesulfonylamino groups, and benzenesulfonylamino groups.

Nonlimiting examples of the sulfamoyl group include C0-C20 sulfamoyl groups. In some embodiments, for example, the sulfamoyl group is a C0-C16 sulfamoyl group. In other embodiments, the sulfamoyl group is selected from C0-C12 sulfamoyl groups. Nonlimiting examples of the sulfamoyl group include sulfamoyl groups, methylsulfamoyl groups, dimethylsulfamoyl groups, and phenylsulfamoyl groups.

Nonlimiting examples of the carbamoyl group include C1-C20 carbamoyl groups. In some embodiment, for example, the carbamoyl group is a C1-C16 carbamoyl group. In other embodiments, the carbamoyl group is selected from C1-C12 carbamoyl groups. Nonlimiting examples of the carbamoyl group include carbamoyl groups, methylcarbamoyl groups, diethylcarbamoyl groups, and phenylcarbamoyl groups.

Nonlimiting examples of the alkylthio group include C1-C20 alkylthio groups. In some embodiments, for example, the alkylthio group is a C1-C16 alkylthio group. In other embodiments, the alkylthio group is selected from C1-C12 alkylthio groups. Nonlimiting examples of the alkylthio group include methylthio groups, and ethylthio groups.

Nonlimiting examples of the arylthio group include C6-C20 arylthio groups. In some embodiments, for example, the arylthio group is a C6-C16 arylthio group. In other embodiments, the arylthio group is selected from C6-C12 arylthio groups. One nonlimiting example of the arylthio group is a phenylthio group.

Nonlimiting examples of the sulfonyl group include C1-C20 sulfonyl groups. In some embodiments, for example, the sulfonyl group is a C1-C16 sulfonyl group. In other embodiments, the sulfonyl group is selected from C1-C12 sulfonyl groups. Nonlimiting examples of the sulfonyl group include mesyl groups, and tosyl groups.

Nonlimiting examples of the sulfinyl group include C1-C20 sulfinyl groups. In some embodiments, for example, the sulfinyl group is a C1-C16 sulfinyl group. In other embodiments, the sulfinyl group is selected from C1-C12 sulfinyl groups. Nonlimiting examples of the sulfinyl group include methanesulfinyl groups, and benzenesulfinyl groups.

Nonlimiting examples of the ureide group include C1-C20 ureide groups. In some embodiments, for example, the ureide group is a C1-C16 ureide group. In other embodiments, the ureide group is selected from C1-C12 ureide groups. Nonlimiting examples of the ureide group include ureide groups, methylureide groups, and phenylureide groups.

Nonlimiting examples of the phosphoricamide group include C1-C20 phosphoricamide group. In some embodiments, for example, the phosphoricamide group is a C1-C16 phosphoricamide group. In other embodiments, the phosphoricamide group is selected from C1-C12 phosphoricamide groups. Nonlimiting examples of the phosphoricamide group include diethylphosphoricamide groups, and phenylphosphoricamide groups.

Nonlimiting examples of the halogen atom include fluorine atoms, chlorine atoms, bromine atoms and iodine atoms.

The heterocyclic group may be a C1-C30 heterocyclic group. In some embodiments, for example, the heterocyclic group is a C1-C15 heterocyclic group. Nonlimiting examples of the heterocyclic group include imidazolyl groups, pyridyl groups, quinolyl groups, furyl groups, thienyl groups, piperidyl groups, morpholino groups, benzoxazolyl groups, benzimidazolyl groups, benzothiazolyl groups, and carbazolyl groups, in which the hetero atom may be nitrogen, oxygen, or sulfur.

Nonlimiting examples of the silyl group include C3-C40 silyl groups. In some embodiments, for example, the silyl group is a C3-C30 silyl group. In other embodiments, the silyl group is selected from C3-C24 silyl groups. Nonlimiting examples of the silyl group include trimethylsilyl groups and triphenylsilyl groups.

In some embodiments of the present invention, the heterocyclic compound represented by Formula 1 may include a compound selected from compounds represented by Formulae 2 through 4 below:

Formula 2

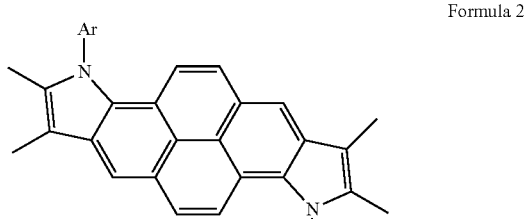

In Formula 2, Ar may be selected from substituted and unsubstituted $C_6$-$C_{60}$ aryl groups, substituted and unsubstituted $C_4$-$C_{60}$ heteroaryl groups, amino groups substituted with at least one substituted or unsubstituted $C_6$-$C_{50}$ aryl group, and substituted and unsubstituted $C_6$-$C_{60}$ condensed polycyclic groups.

Formula 3

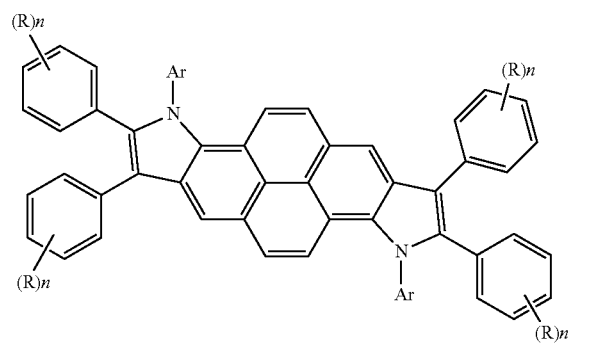

Formula 4

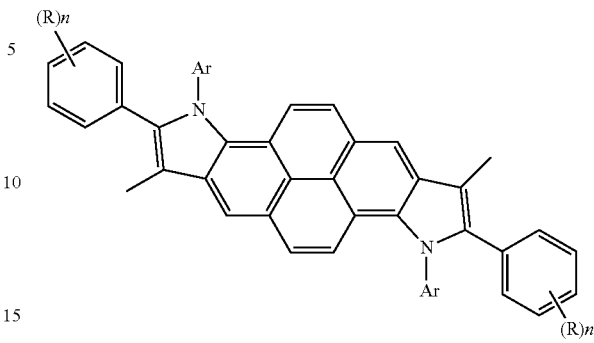

In Formulae 3 and 4, Ar may be selected from substituted and unsubstituted $C_6$-$C_{60}$ aryl groups, substituted and unsubstituted $C_4$-$C_{60}$ heteroaryl groups, amino groups substituted with at least one substituted or unsubstituted $C_6$-$C_{50}$ aryl group, and substituted and unsubstituted $C_6$-$C_{60}$ condensed polycyclic groups. R may be selected from hydrogen atoms, heavy hydrogen atoms, $C_1$-$C_{20}$ alkyl groups, $C_1$-$C_{20}$ alkoxygroups, $C_1$-$C_{20}$ alkoxycarbonyl groups, $C_6$-$C_{20}$ aryl groups, $C_6$-$C_{20}$ aryloxy groups, $C_6$-$C_{20}$ arylthio groups, amino groups substituted with at least one $C_6$-$C_{20}$ aryl group, $C_3$-$C_{20}$ carbocyclic groups, $C_4$-$C_{20}$ heteroaryl groups, $C_4$-$C_{20}$ heterocyclic groups, $C_6$-$C_{20}$ condensed polycyclic groups, halogen atoms, cyano groups, hydroxyl groups, and carboxyl groups. In some embodiments, at least two substituents may combine to form an aromatic ring. Also, n may be an integer from 1 to 5.

According to some embodiments, in Formulae 2 through 4, Ar may be selected from monocyclic to tricyclic aryl or heteroaryl groups. Nonlimiting examples of monocyclic to tricyclic aryl or heteroaryl groups include phenyl groups, naphthyl groups, biphenyl groups, terphenyl groups, fluorenyl groups, and carbazolyl groups. The monocyclic to tricyclic aryl or heteroaryl group may be substituted with one to three substituents. Nonlimiting examples of these substituents include C1-C5 alkyl groups, C1-5 alkoxy groups, cyano groups, amino groups, phenoxy groups, phenyl groups, and halogen atoms.

In Formula 1, and Formulae 2 through 4, Ar may be selected from the below groups, but is not limited thereto:

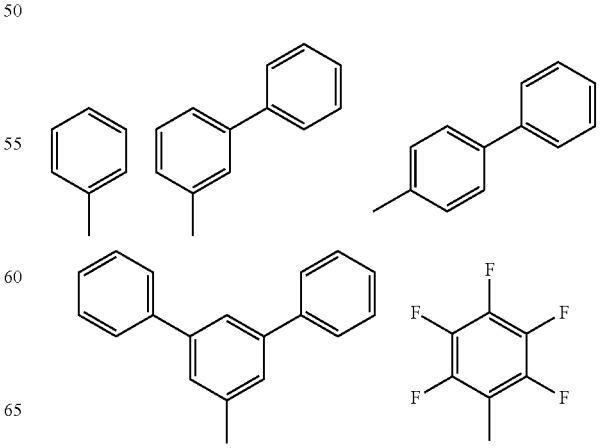

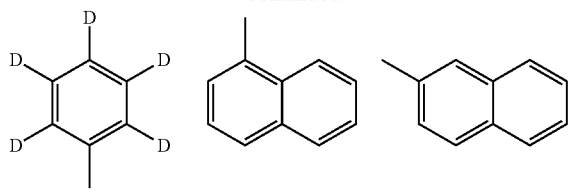
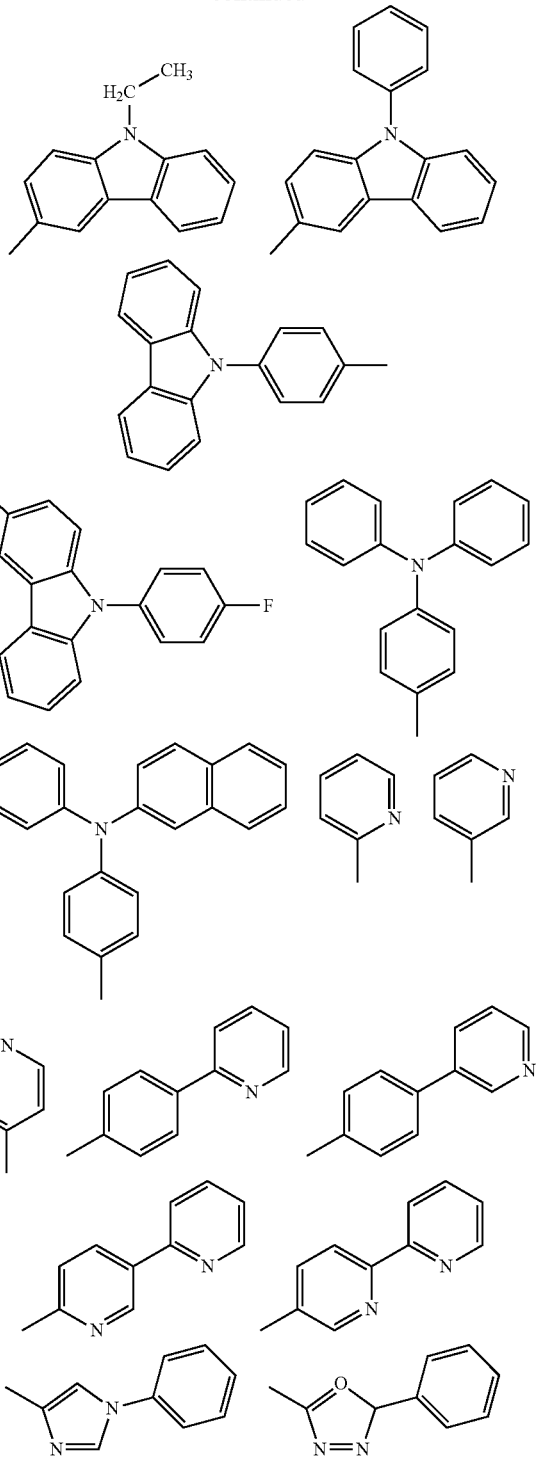
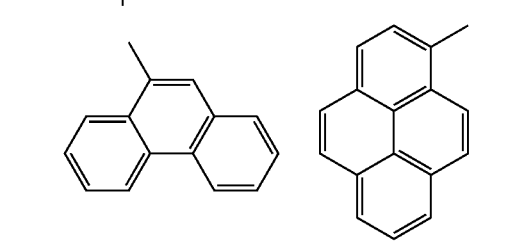
In Formula 1, each of $R_1$ through $R_5$ may be independently selected from one of the below monovalent organic groups, but is not limited thereto:
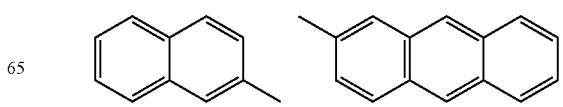

-continued

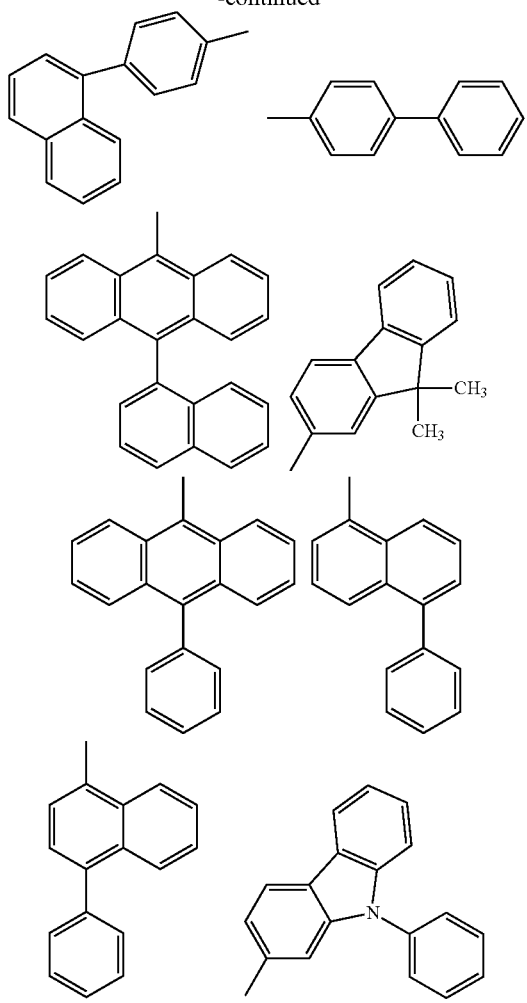

In Formulae 3 or 4,

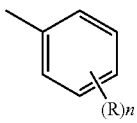

may be a phenyl group, a naphthyl group, or an anthracenyl group.

Hereinafter, substituents described with reference to Formulae 1 through 4 will be described.

The unsubstituted $C_1$-$C_{50}$ alkyl group may be linear or branched. Nonlimiting examples of the alkyl group include methyl groups, ethyl groups, propyl groups, isobutyl groups, sec-butyl groups, pentyl groups, iso-amyl groups, hexyl groups, heptyl groups, octyl groups, nonanyl groups, and dodecyl groups. At least one hydrogen atom of the alkyl group may be substituted with a substituent selected from heavy hydrogen atoms, halogen atoms, hydroxyl groups, nitro groups, cyano groups, amino groups, amidino groups, hydrazines, hydrazones, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

The unsubstituted $C_3$-$C_{50}$ carbocyclic group refers to a $C_3$-$C_{50}$ cycloalkyl group where at least one hydrogen atom in the carbon ring may be substituted with the substituents described above in connection with the $C_1$-$C_{50}$ alkyl group.

The unsubstituted $C_4$-$C_{60}$ heterocyclic group refers to a $C_4$-$C_{60}$ cycloalkyl group including one, two or three hetero atoms selected from N, O, P and S, where at least one hydrogen atom in the heterocyclic group may be substituted with the substituents described above in connection with the $C_1$-$C_{50}$ alkyl group.

The unsubstituted $C_1$-$C_{50}$ alkoxy group is a group having a —OA structure where A is an unsubstituted $C_1$-$C_{50}$ alkyl group as described above. Nonlimiting examples of the alkoxy group include methoxy groups, ethoxy groups, propoxy groups, isopropyloxy groups, butoxy groups, and pentoxy groups. At least one hydrogen atom of the alkoxy group may be substituted with the substituents described above in connection with the $C_1$-$C_{50}$ alkyl group.

The unsubstituted $C_6$-$C_{60}$ aryl group refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the substituents described above in connection with the $C_1$-$C_{50}$ alkyl group.

Nonlimiting examples of the substituted or unsubstituted $C_6$-$C_{60}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-tolyl groups, o-, m-, and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$ heteroaryl group includes one, two or three hetero atoms selected from N, O, P and S. At least two rings may be fused to each other or linked to each other by a single bond. Nonlimiting examples of the unsubstituted $C_4$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. At least one hydrogen atom in the heteroaryl group may be substituted with the substituents described above in connection with the $C_1$-$C_{50}$ alkyl group.

The unsubstituted $C_6$-$C_{60}$ condensed polycyclic group refers to a substituent including at least two rings where at least one aromatic ring and/or at least one non-aromatic ring are fused to each other. The unsubstituted $C_6$-$C_{60}$ polycyclic condensed group may include some of the substituents described in connection with the aryl group or the heteroaryl group.

The heterocyclic compound of Formula 1 may be used as an organic layer material having at least one of electron-injecting capability, electron-transporting capability, and light-emitting capability.

The heterocyclic compound of Formula 1 has a high glass transition temperature (Tg) or melting point due to the introduction of the heterocyclic group. Thus, the heterocyclic compound has high heat resistance against Joule's heat generated in an organic layer, between organic layers, or between an organic layer and a metallic electrode when light emission occurs. The heterocyclic compound also has high durability in a high-temperature environment. An organic light-emitting device manufactured using the heterocyclic compound has high durability when stored or operated.

Nonlimiting examples of the heterocyclic compound of Formula 1 include the following Compounds I-54:

1
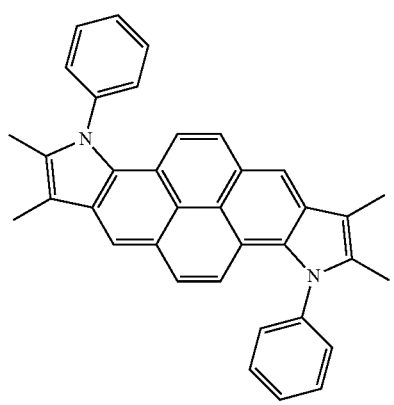

2
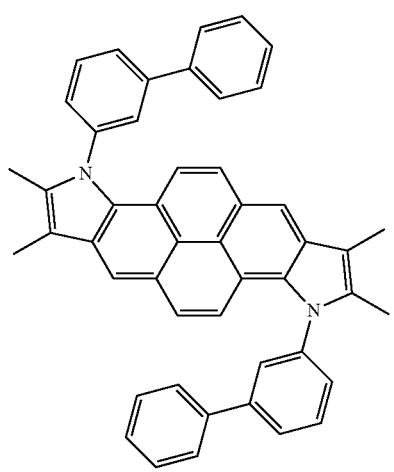

-continued

3
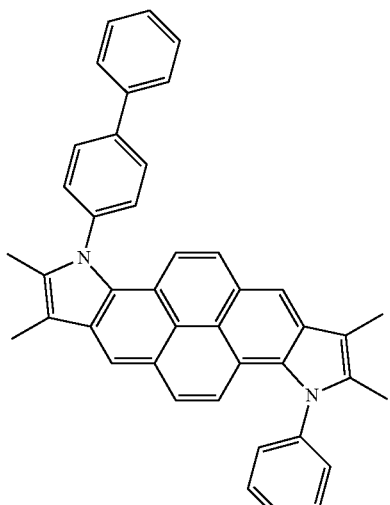

4
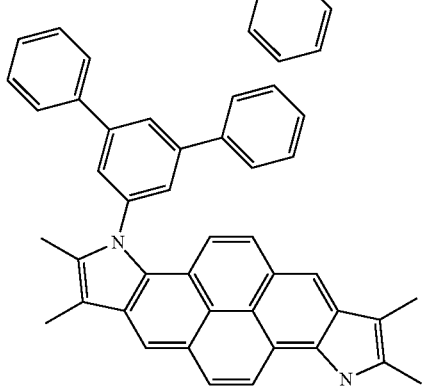

5
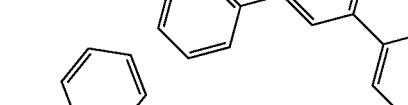
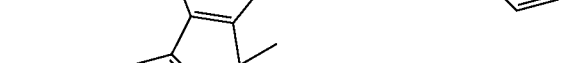

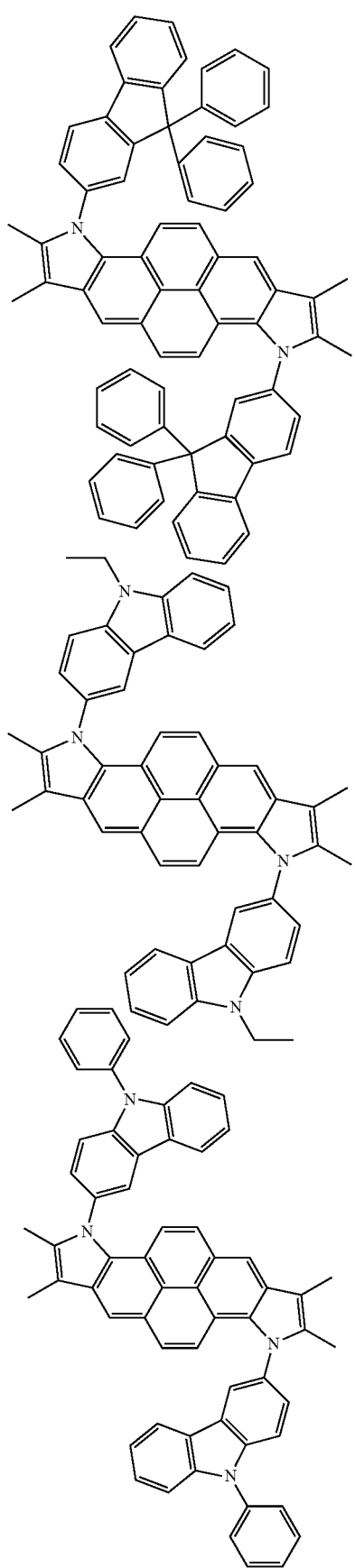
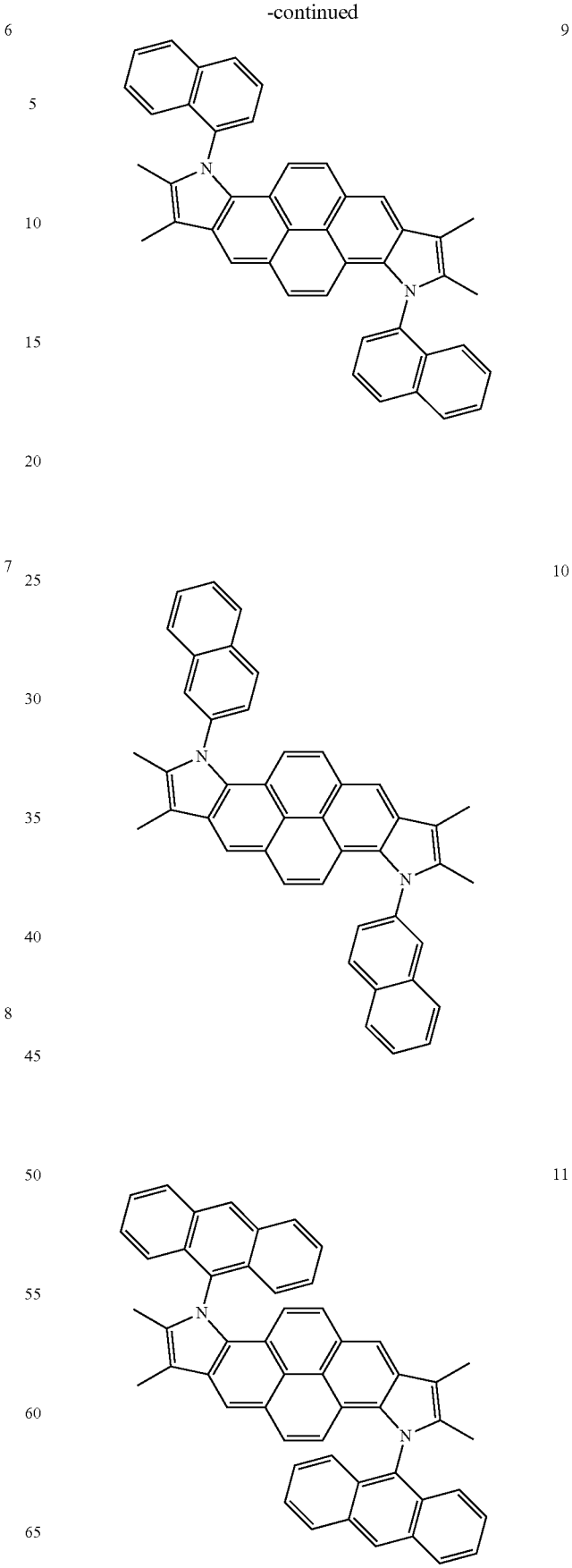

12
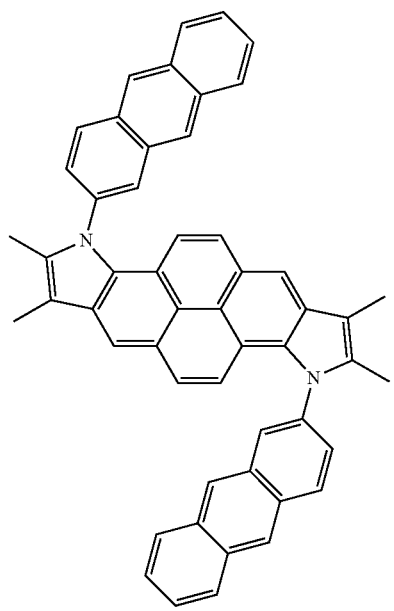
14
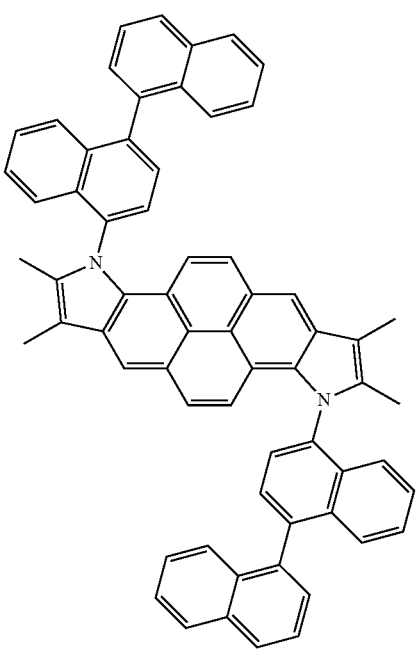
13
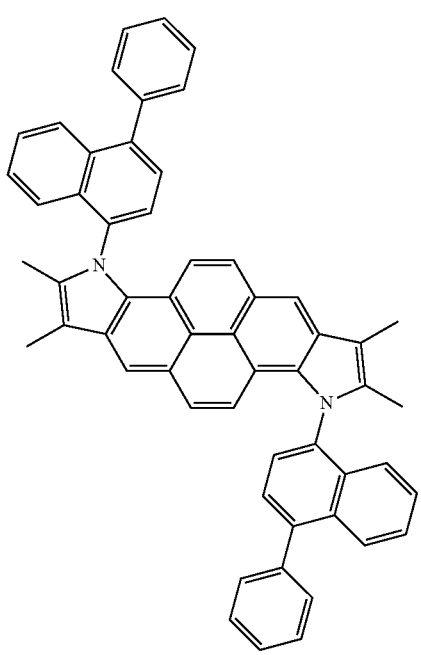
15
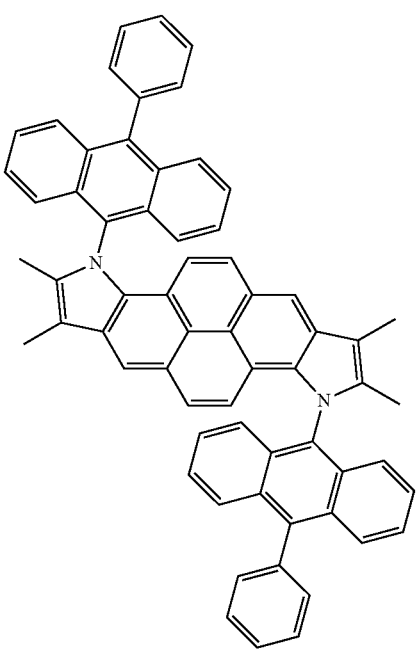

16
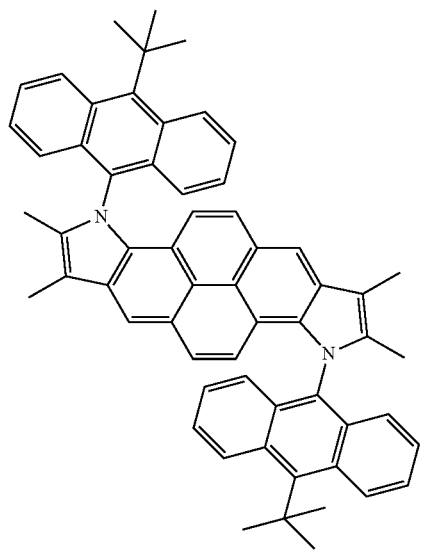
17
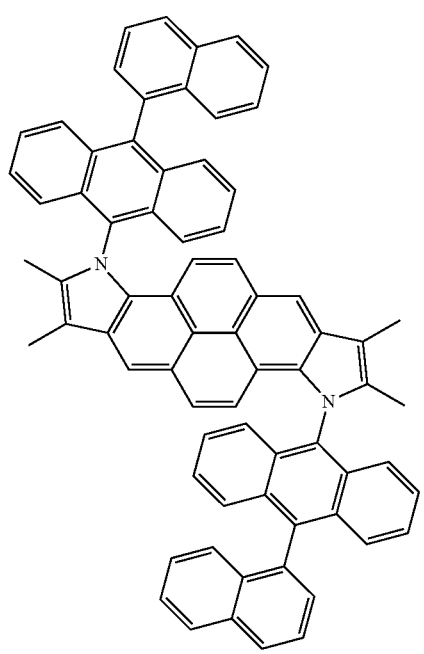
18
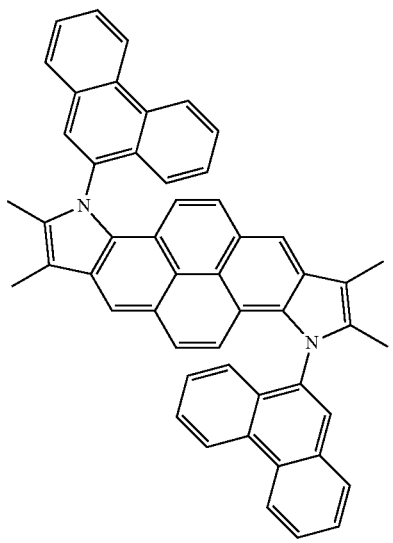
19
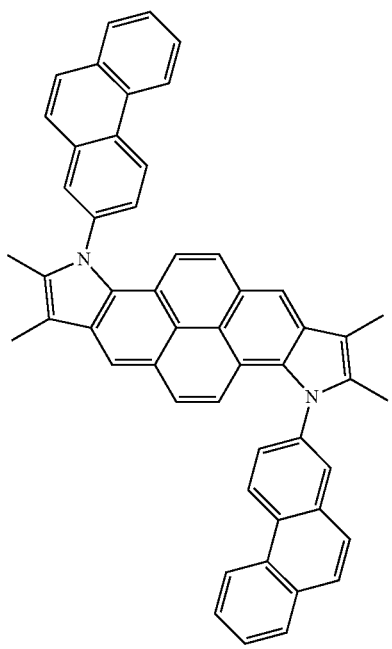

20
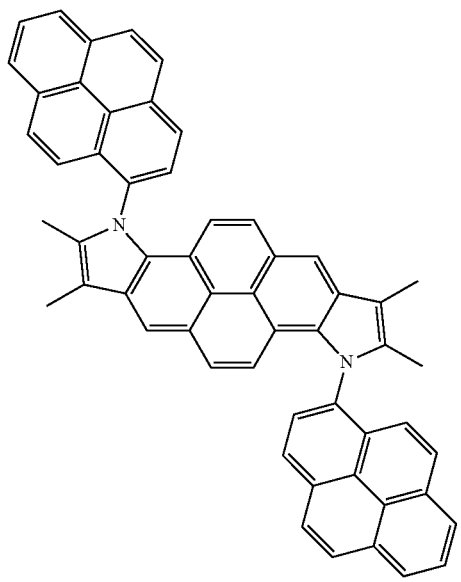
5
10
15
20
25
30
35
21
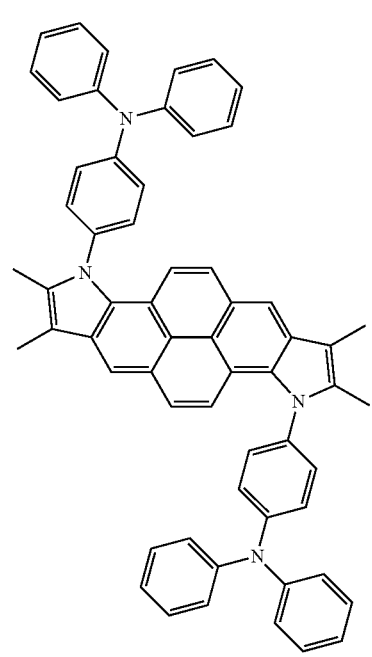
40
45
50
55
60
65
22
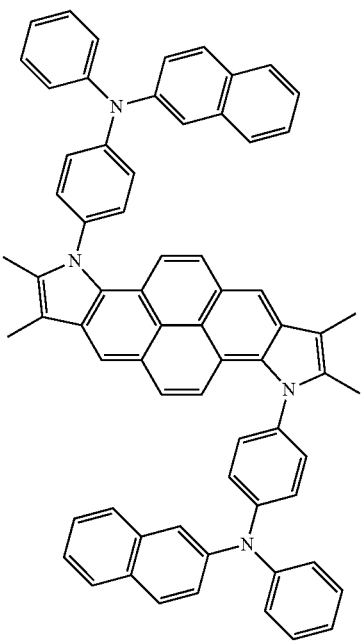
23
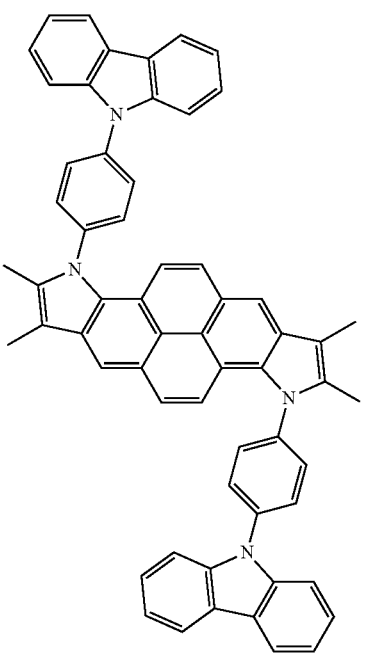

23
-continued
24
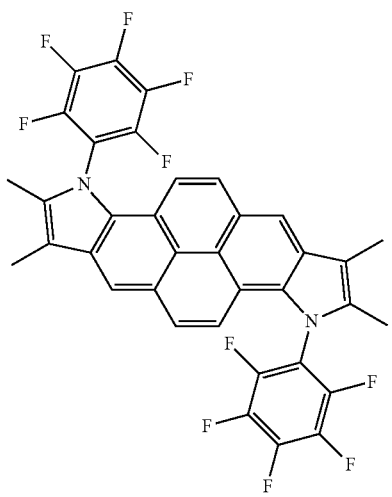
25
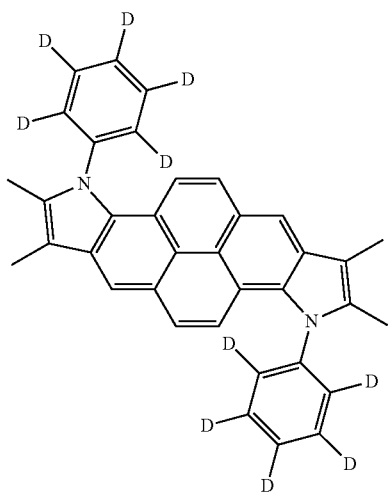
26
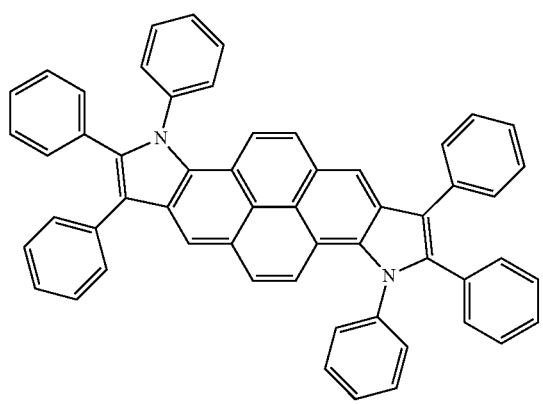
24
-continued
27
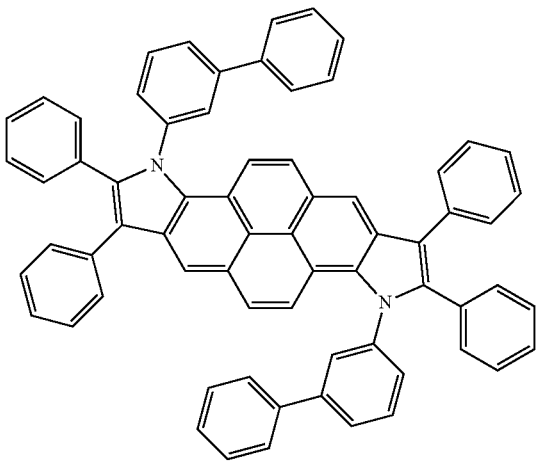
28
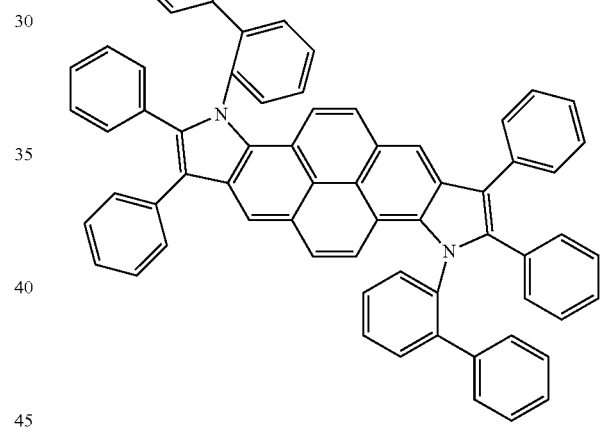
29
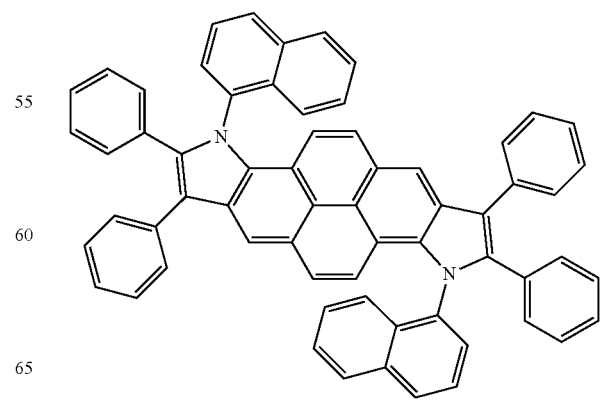

25
-continued
30
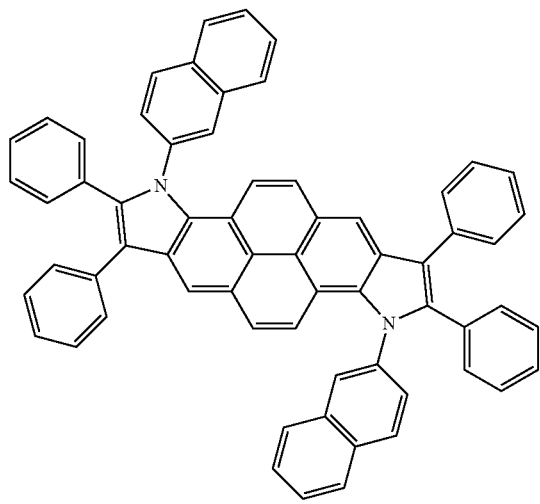
31
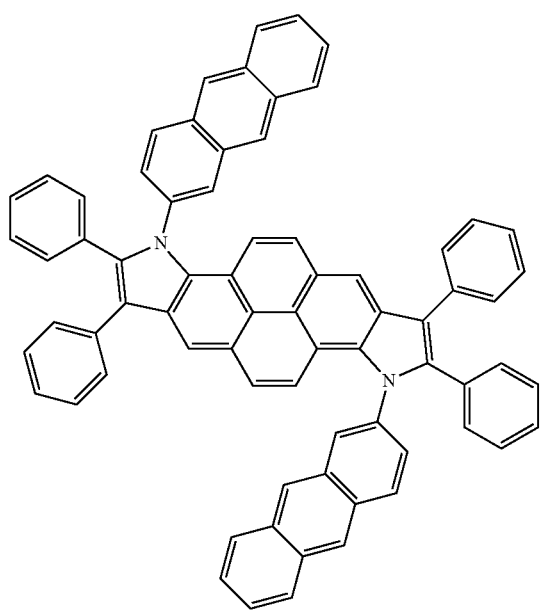
32
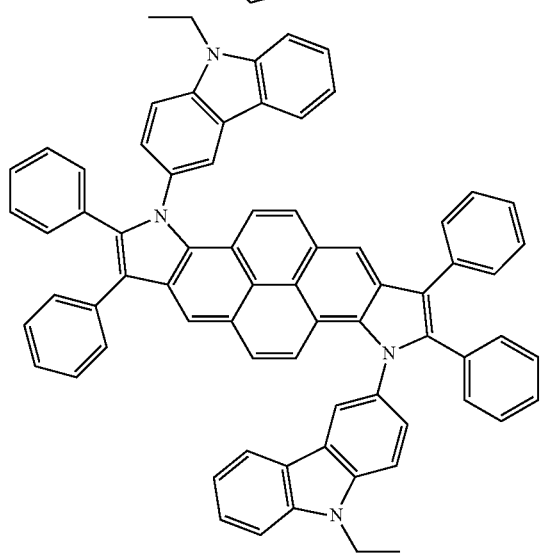
26
-continued
33
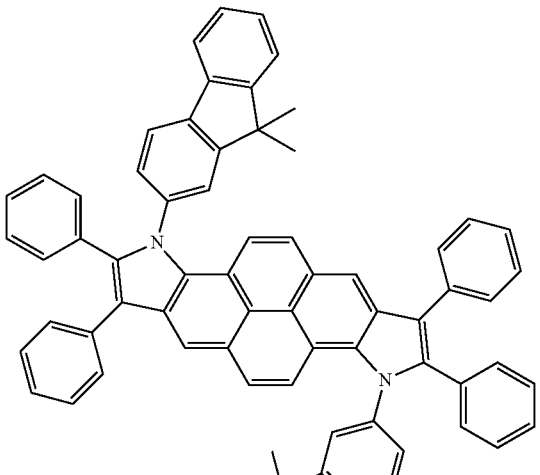
34
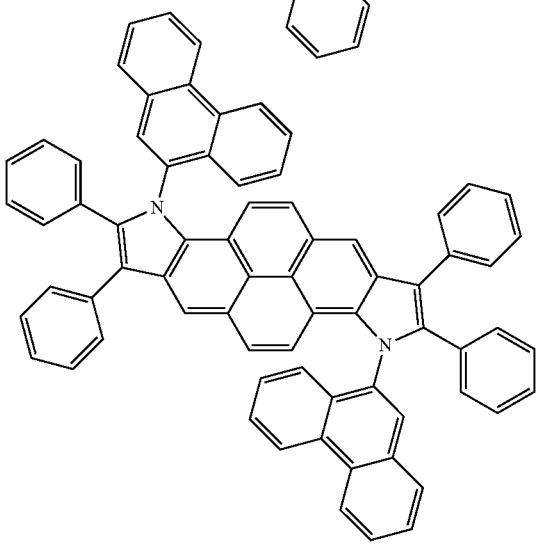
35

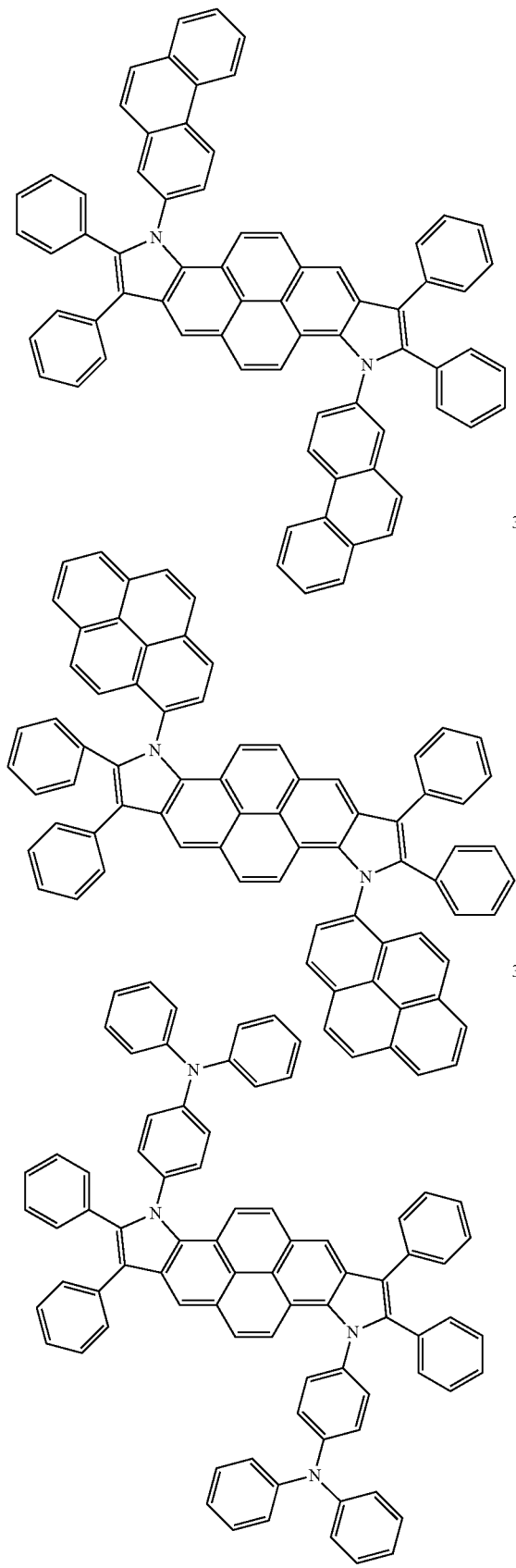
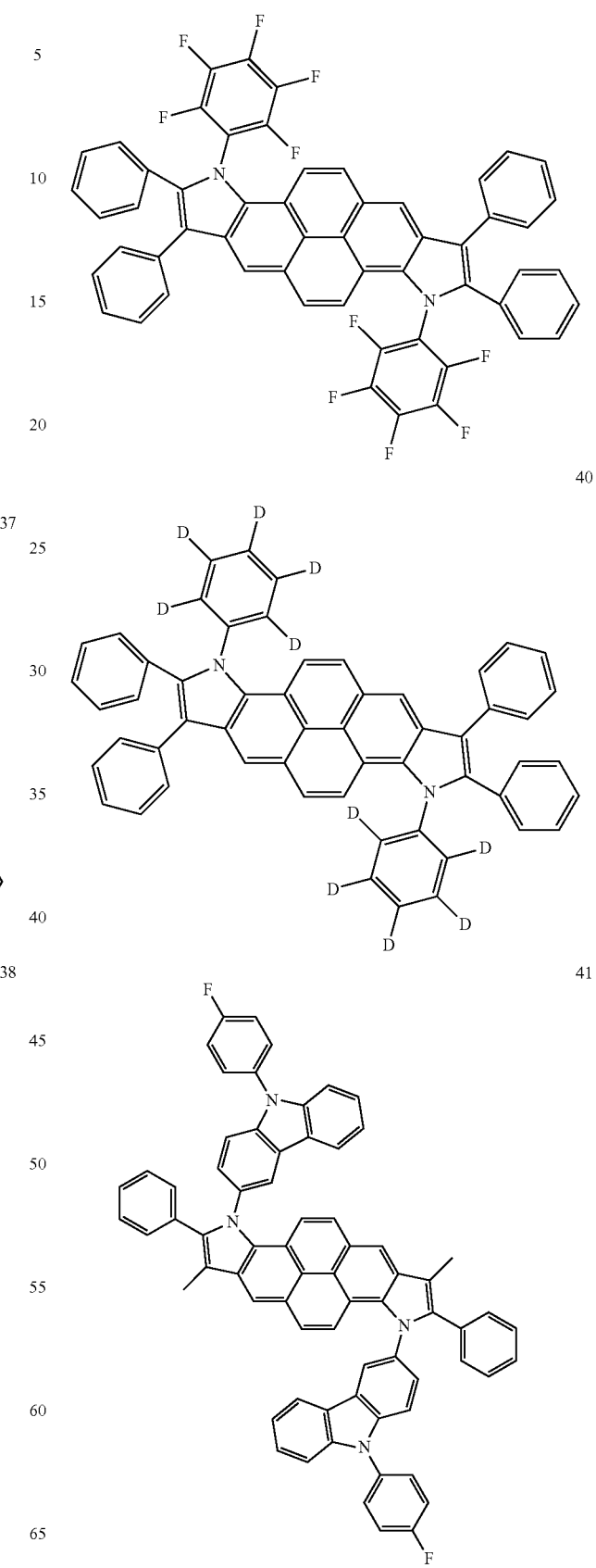

42
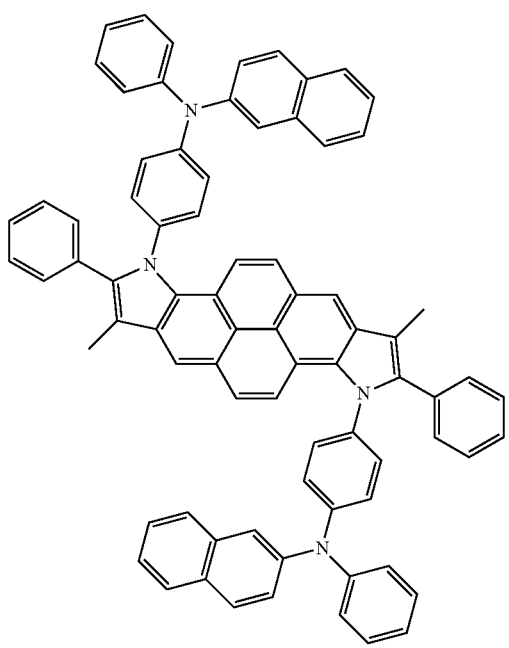
43
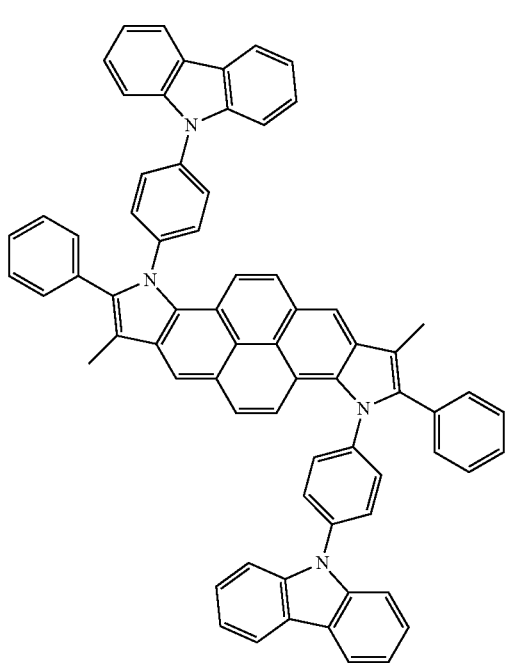
44
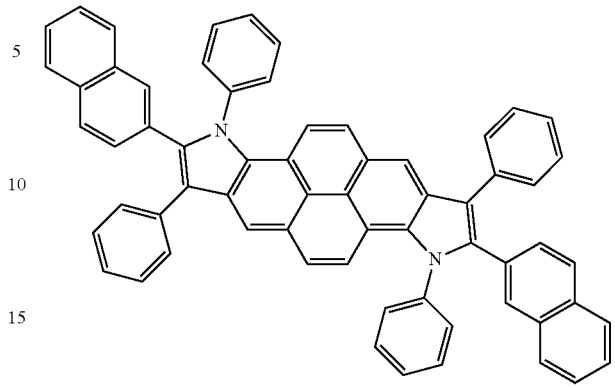
45
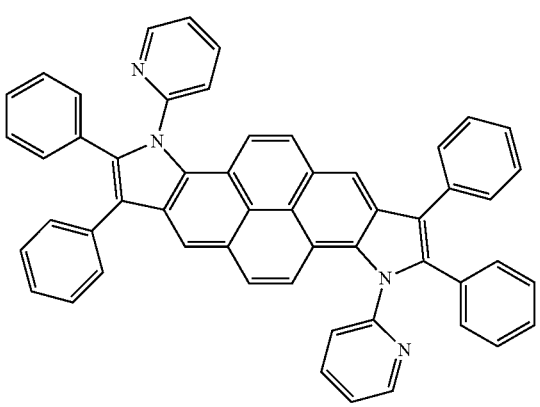
46

47
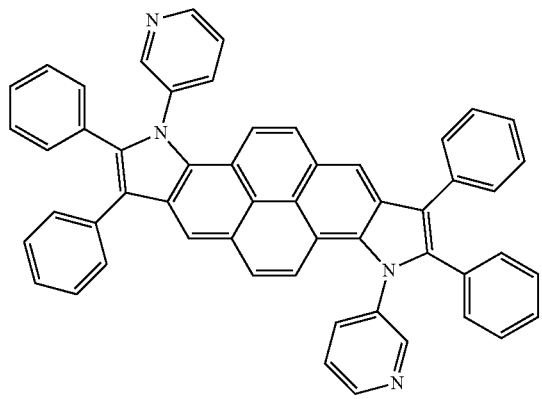
48
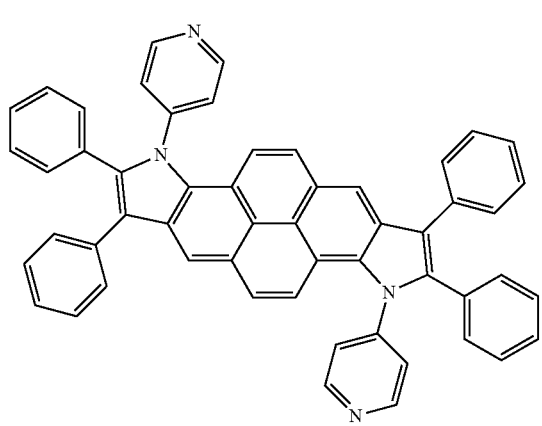
49
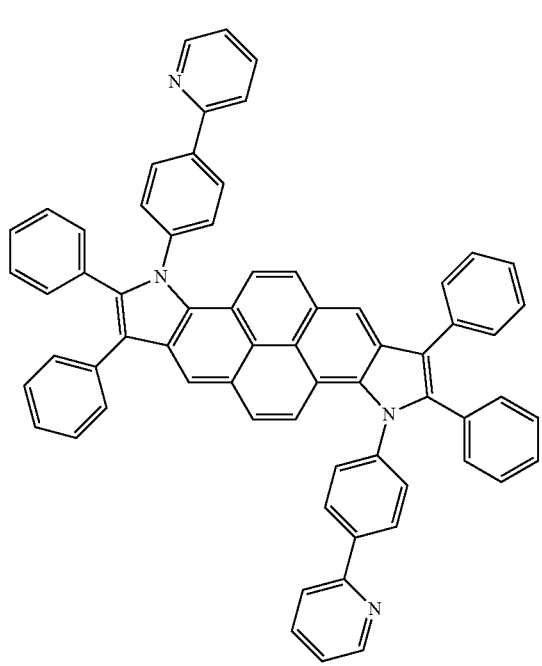
50
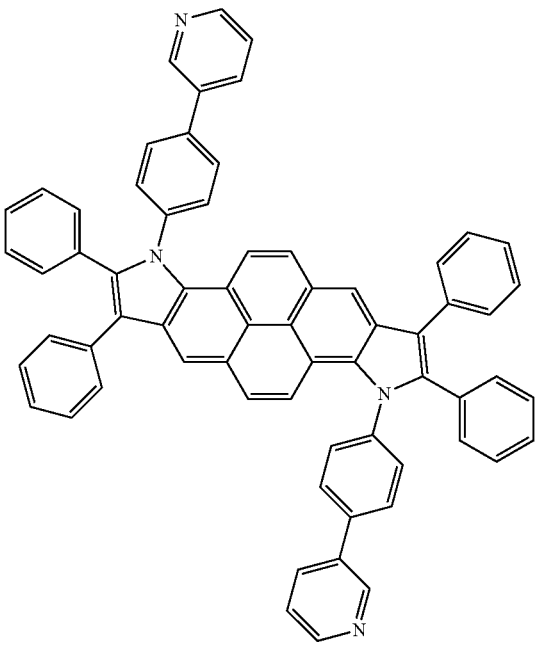
51
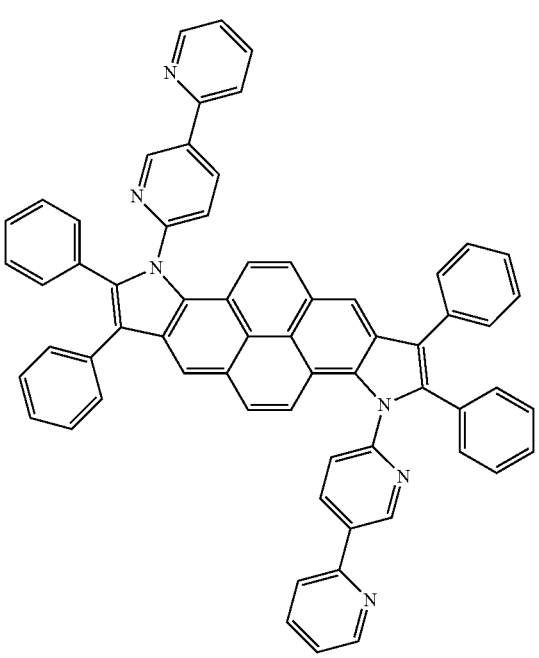

52
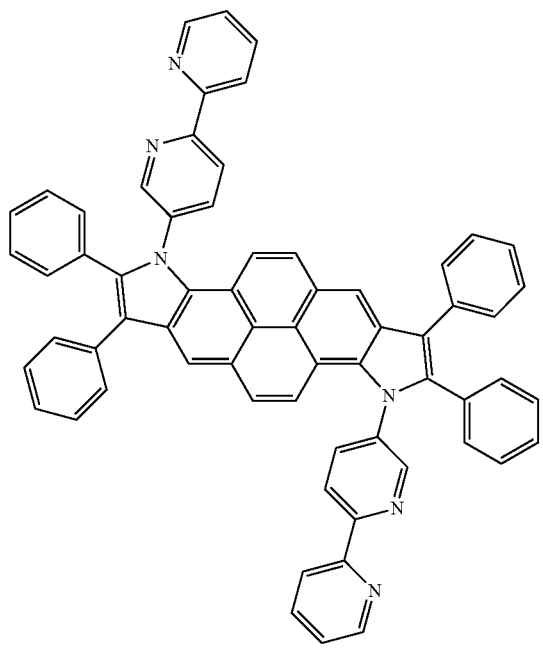
53
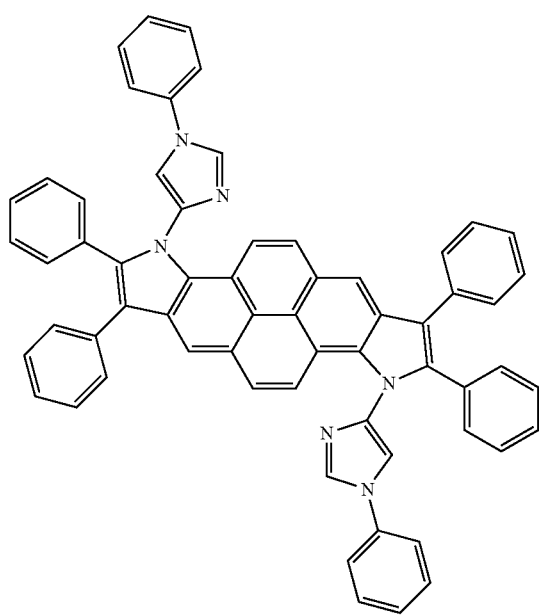
54
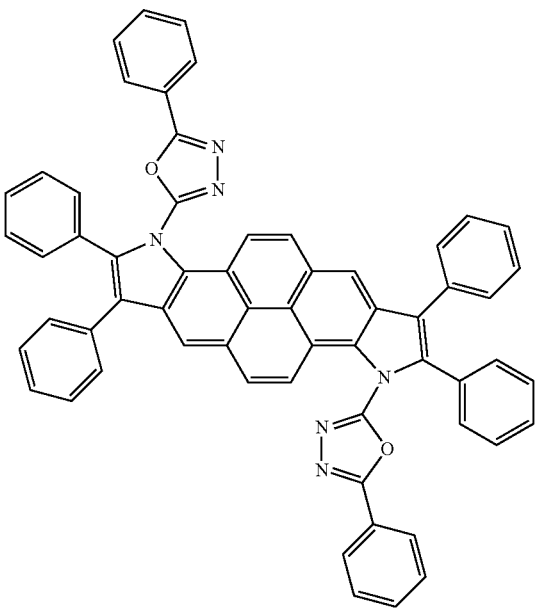
In some embodiments, for example, the heterocyclic compound of Formula 1 is selected from Compound 5, Compound 8, Compound 21, Compound 26, Compound 30, and Compound 47.
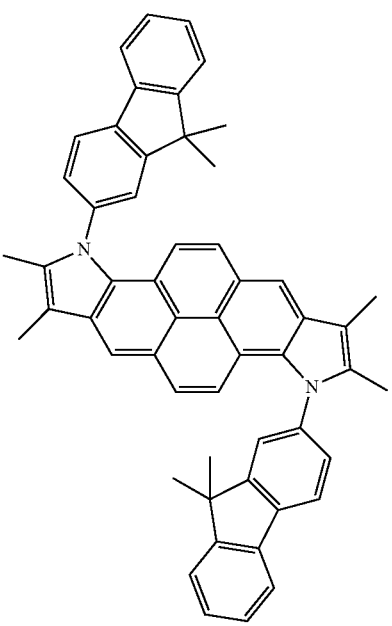

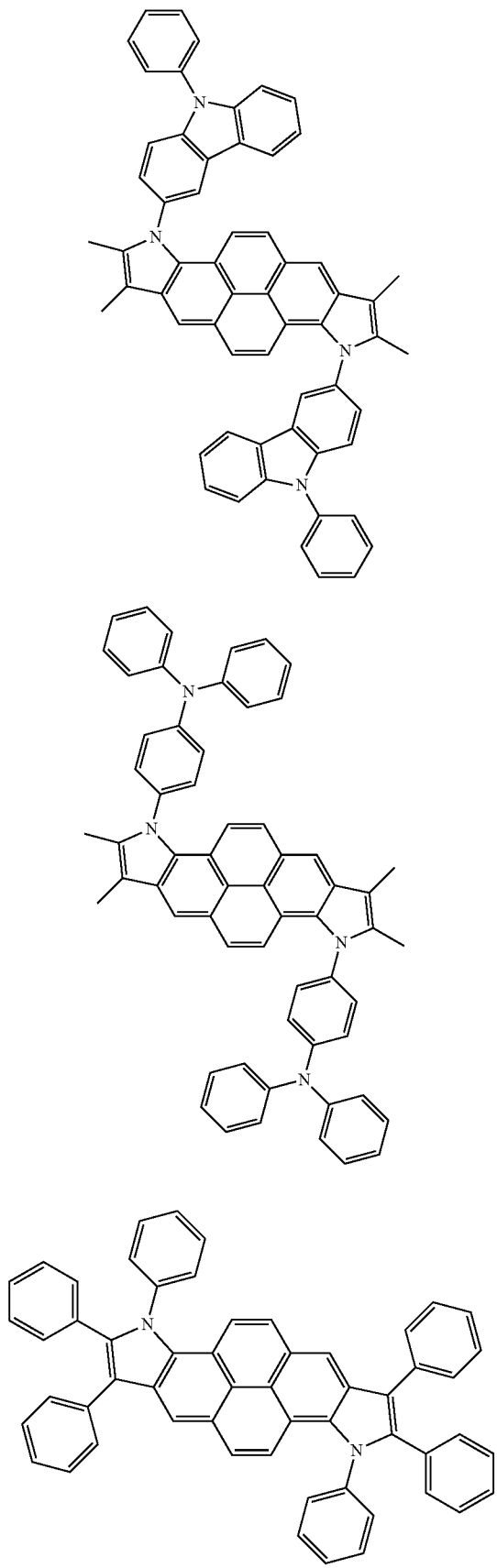
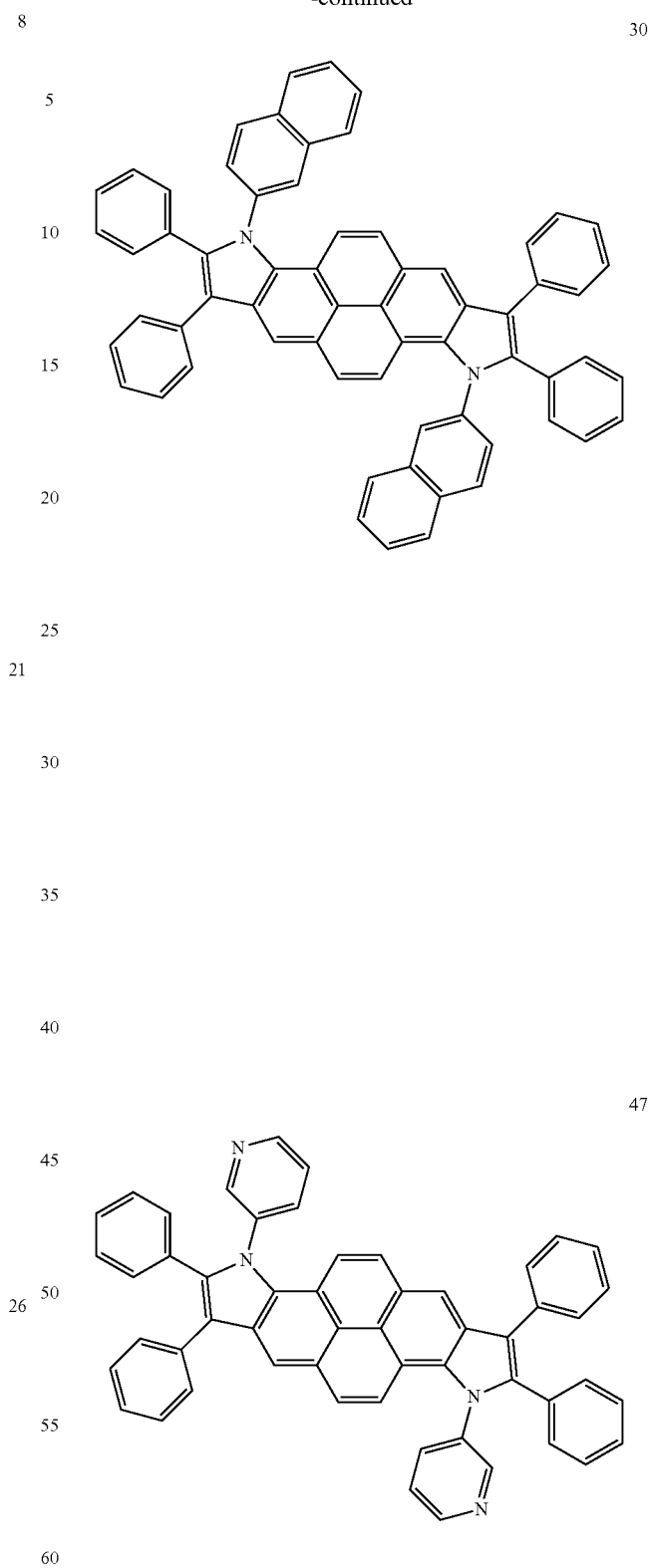
According to other embodiments of the present invention, a method of synthesizing a heterocyclic compound of Formula 1 is provided. First, a heterocyclic compound of Formula 5 is prepared according to the following reaction scheme.

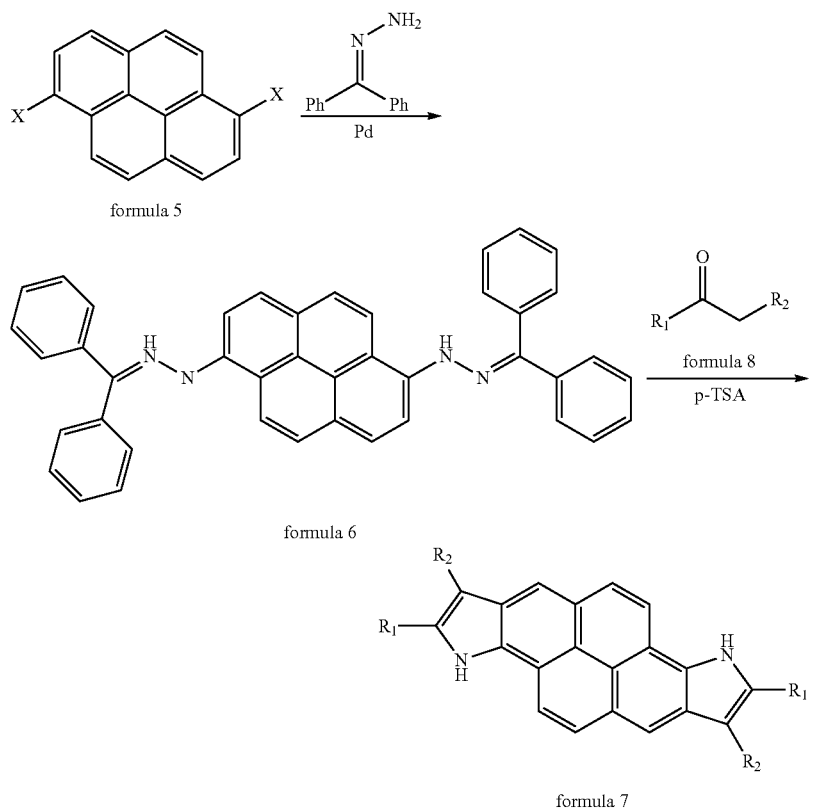

formula 5 formula 6 formula 7

In the above reaction scheme, X is a halogen atom, and $R_1$ and $R_2$ are as defined above with reference to Formula 1. As illustrated in the reaction scheme, benzophenone hydrazone, sodium butoxide, palladium diacetate, and 2-dicyclohexylphospino-2',4',6'-triisopropylbiphenyl are added to a heterocyclic compound represented by Formula 5. The components are mixed together and heated to obtain a compound represented by Formula 6.

In the synthesis method, the amount of benzophenone hydrazone may be about 1.05 to about 1.2 moles based on 1 mole of the heterocyclic compound of Formula 5. The amount of sodium butoxide may be about 1.2 to about 1.5 moles based on 1 mole of the heterocyclic compound of Formula 5. The amount of palladium diacetate may be about 0.02 to about 0.05 moles, and the amount of 2-dicyclohexylphospino-2',4', 6'-triisopropylbiphenyl may be about 0.02 to about 0.05 moles, based on 1 mole of the heterocyclic compound of Formula 5.

The heating may be performed at a temperature of about 80° C. to about 100° C. When the heating temperature is outside this range, a low yield of the compound of Formula 6 may be obtained.

Then, the compound of Formula 6 is mixed with p-toluenesulfonic acid monohydrate and the compound represented by Formula 8, and the mixture is heated to obtain a compound represented by Formula 7.

When the reaction is completed, the reaction product is worked up to obtain the heterocyclic compound of Formula 7.

The heating temperature may be about 60° C. to 100° C. When the heating temperature is outside this range, a low yield of the compound of Formula 7 may be obtained.

The amount of p-toluenesulfonic acid monohydrate may be about 1.5 to about 2.0 moles, and the amount of the compound represented by Formula 8 may be about 1.5 to about 2.0 moles, based on 1 mole of the compound of Formula 6. The compound of Formula 8 may be benzylphenylketone According to other embodiments of the present invention, an organic light-emitting device includes a first electrode, a second electrode, and an organic layer between the first electrode and the second electrode. The organic layer includes at least one organic layer containing the heterocyclic compound of Formula 1 described above. The heterocyclic compound may be used exclusively or may be included in a mixture.

The at least one organic layer containing the heterocyclic compound of Formula 1 may include an electron injection layer, an electron transport layer, or a single layer having both electron injection and electron transport capabilities. The at least one organic layer containing the heterocyclic compound of Formula 1 may include an emission layer. The heterocyclic compound of Formula 1 may be used as a host material for a blue, green, or red fluorescent or phosphorescent material.

In some embodiments, for example, the at least one organic layer containing the heterocyclic compound represented by Formula 1 may include an electron injection layer or an electron transport layer.

The organic layer may include an emission layer, an electron transport layer, and an electron injection layer, where the electron injection layer or the electron transport layer may contain the heterocyclic compound of Formula 1, and the emission layer may contain an anthracene compound.

Alternatively, the organic layer may include an emission layer, an electron transport layer, and an electron injection layer, where the electron injection layer or the electron transport layer may contain the heterocyclic compound of Formula 1, and the emission layer may contain a $C_4$-$C_{60}$ heteroaryl compound or a styryl compound.

The first electrode may be an anode, and the second electrode may be a cathode, but the reverse is also possible.

The organic light-emitting device described above may also include at least one layer selected from a hole injection layer, a hole transport layer, an electron blocking layer, an emission layer, a hole blocking layer, an electron transport layer and an electron injection layer. These organic layers may have double-layered structures.

An organic light-emitting device according to embodiments of the present invention may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. An organic light-emitting device according other embodiments may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure. An organic light-emitting device according yet other embodiments may have a first electrode/hole injection layer/hole transport layer/emission layer/single layer having both electron transport and electron injection capabilities/second electrode structure, or a first electrode/single layer having both hole injection and hole transport capabilities/emission layer/single layer having both electron transport and electron injection capabilities/second electrode structure.

An organic light-emitting device according to embodiments of the present invention may have various structures, such as a top emission type organic light-emitting device structure or a bottom emission type organic light-emitting device structure.

According to embodiments of the present invention, a method of manufacturing an organic light-emitting device is provided. FIG. 1 illustrates the structure of an organic light-emitting device according to an embodiment of the present invention. Referring to FIG. 1, the organic light-emitting device includes a substrate, a first electrode (anode), a hole injection layer (HIL), a hole transport layer (HTL), an emission layer (EML), an electron transport layer (ETL), an electron injection layer (EIL), and a second electrode (cathode).

The first electrode is formed on the substrate by deposition or sputtering. The first electrode may be formed of a first electrode material having a high work function. The first electrode may be an anode or a cathode. The substrate may be any substrate conventionally used in organic light-emitting devices, and may be, for example, a glass substrate or a transparent plastic substrate having good mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

A HIL may be formed on the first electrode by vacuum deposition, spin coating, casting, Langmuir Blodgett (LB) deposition, or the like. When the HIL is formed by vacuum deposition, the vacuum deposition conditions may vary according to the compound used to form the HIL and the desired structure and thermal properties of the HIL to be formed. In general, however, the vacuum deposition may be performed at a deposition temperature of about 100° C. to about 500° C., under a pressure of about $10^{-8}$ torr to about $10^{-3}$ torr, at a deposition speed of about 0.01 to about 100 Å/sec, and to a layer thickness of about 10 Å to about 5 μm.

When the HIL is formed by spin coating, the coating conditions may vary according to the compound used to form the HIL and the desired structure and thermal properties of the HIL to be formed. In general, however, the coating speed may be about 2000 rpm to about 5000 rpm, and the temperature for heat treatment (performed to remove the solvent after coating) may be about 80° C. to about 200° C.

Any known HIL material may be used. Nonlimiting examples of HIL materials include to form the HIL. Nonlimiting examples of HIL materials include phthalocyanine compounds (such as copper phthalocyanine), star-burst type amine derivatives (such as TCTA, 4,4',4"-tris(3-methylphenylphenylamino)triphenylamine (m-MTDATA), N,N'-di(1-naphthyl)-N,N'-diphenylbenzidine) (NPB), TDATA, and 2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and (polyaniline)/poly(4-styrenesulfonate) (PANI/PSS).

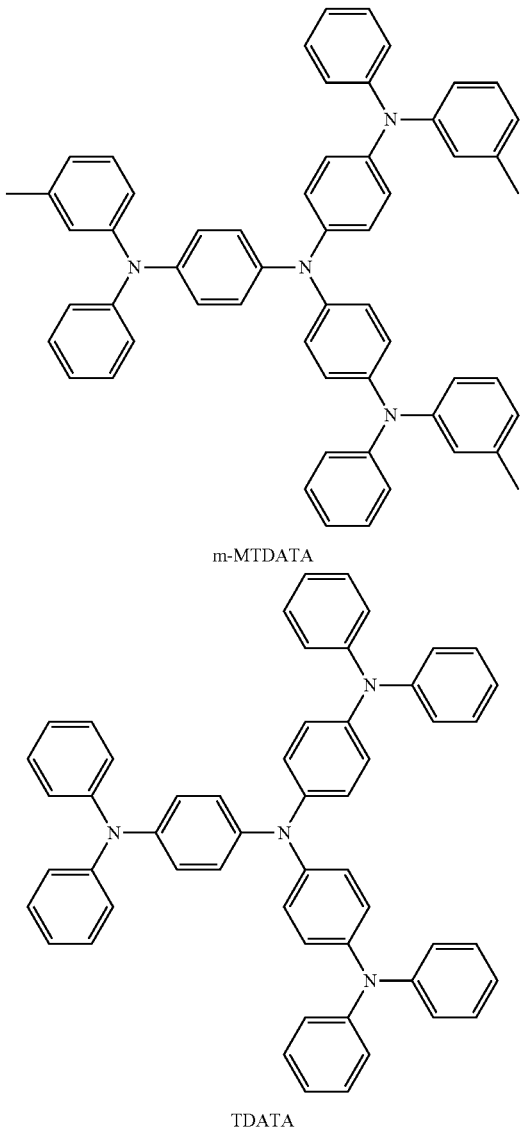

m-MTDATA

TDATA

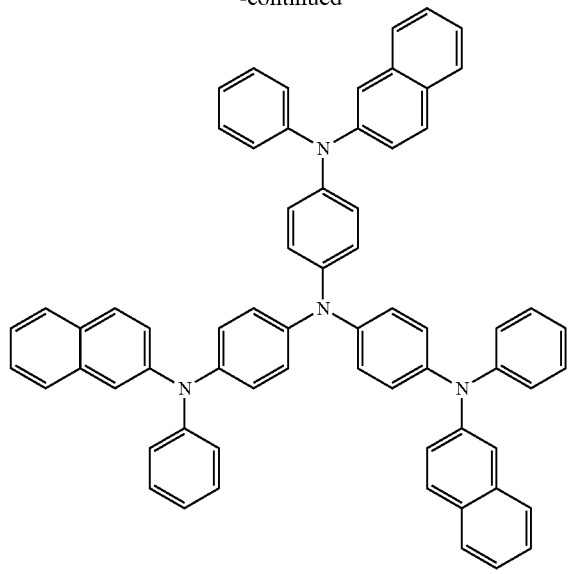

2-TNATA

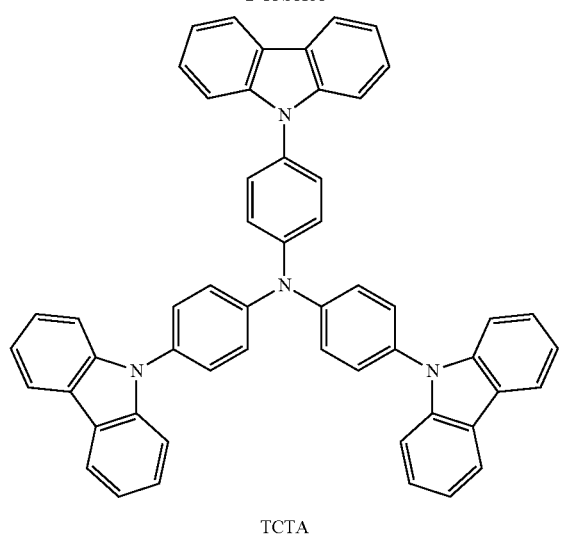

TCTA

The thickness of the HIL may be about 100 to about 10,000 Å. In some embodiments, for example, the thickness of the HIL is about 100 to about 1,000 Å. When the HIL has a thickness within these ranges, the HIL has good hole injection characteristics without increasing driving voltage.

A HTL may be formed on the HIL by vacuum deposition, spin coating, casting, LB deposition, or the like. When the HTL is formed by vacuum deposition or spin coating, the conditions for deposition and coating are similar to those for the formation of the HIL, although the conditions for the deposition and coating may vary according to the material used to form the HTL.

The HTL may be formed of any known material used to form a HTL. Nonlimiting examples of suitable materials for the HTL include carbazole derivatives (such as N-phenylcarbazole and polyvinylcarbazole), and typical amine derivatives having an aromatic condensation ring (such as 4,4'-bis[N-(1-naphthyl)-N-phenylamino]biphenyl (NPB), and N,N'-bis(3-methylphenyl)-N,N'-diphenyl-[1,1-biphenyl]-4,4'-diamine (TPD)).

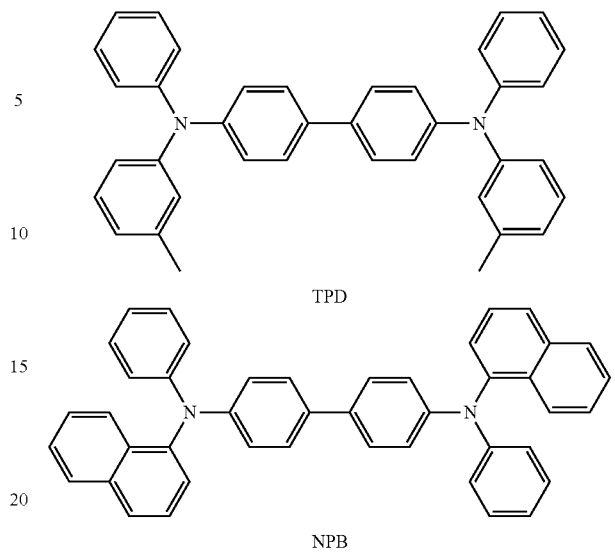

The thickness of the HTL may be about 50 to about 1,000 Å. In some embodiments, for example, the thickness of the HTL is about 100 to about 600 Å. When the HTL has a thickness within these ranges, the HTL has good hole transporting characteristics without substantially increasing driving voltage.

Optionally, an electron blocking layer may be formed on the HTL. The electron blocking layer blocks migration of electrons into the HTL. The electron blocking layer may include, for example, TATT represented by the following formula:

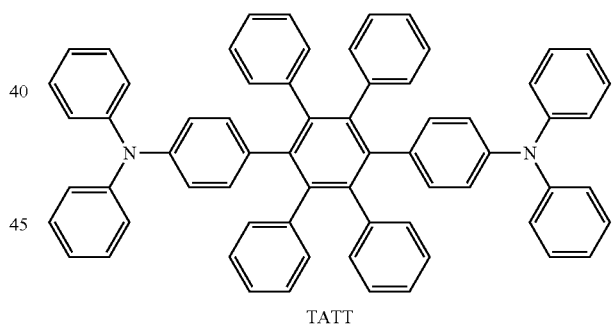

TATT

The thickness of the electron blocking layer may be about 50 to about 200 Å. When the electron blocking layer has a thickness within this range, the electron blocking layer has good electron blocking characteristics without substantially increasing driving voltage.

The EML is formed on the resultant structure. The EML may be formed by vacuum deposition, spin coating, casting, or LB deposition. When the EML is formed by vacuum deposition or spin coating, the conditions for deposition and coating are similar to those for the formation of the HIL, although the conditions for deposition and coating may vary according to the material used to form the EML.

The EML may include the heterocyclic compound of Formula 1. The heterocyclic compound of Formula 1 may be used as a host of the EML. Alternatively, when the heterocyclic compound of Formula 1 is used to form the EIL or the ETL, the EML of the organic light-emitting device may be formed of any suitable light-emitting material for forming the EML of an organic light-emitting device. Nonlimiting examples of suitable light-emitting materials for forming the EML include known hosts and dopants. Dopants used to form the EML may include either a fluorescent dopant or a phosphorescent dopant.

Nonlimiting examples of hosts include Alq$_3$, 4,4'-N,N'-dicarbazole-biphenyl (CPB), poly(n-vinylcarbazole) (PVK), 9,10-di(naphthalene-2-yl)anthracene (ADN), distyrylarylene (DSA), arylamine and heteroarylamine compounds, anthracene compounds having symmetrical or asymmetrical structures, styrylanthracene compounds, pyrene compounds having symmetrical or asymmetrical structures, spirofluorene compounds, and fluorene compounds.

Either a fluorescent dopant or a phosphorescent dopant may be used as the dopant for forming the EML. Nonlimiting examples of the fluorescent dopant include styryl compounds, aryl and heterocyclic compounds, styryl heterocyclic compounds, and aminopyrene compounds. Nonlimiting examples of the phosphorescent dopant include Ir(PPy)$_3$ (PPy=phenylpyridine) (green), F$_2$Irpic, platinum(II) octaethylporphyrin (PtOEP), compound A represented by the following formula, RD 61 (which is a red phosphorescent dopant available from UDC), and metal-complex compounds including iridium (Ir), ruthenium (Ru), palladium (Pd), platinum (Pt), osmium (Os), or rhenium (Re) as a core metal.

compound A

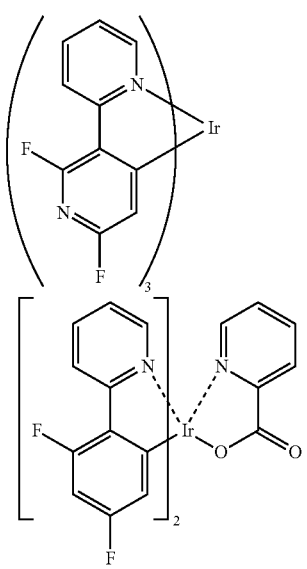

F$_2$Irpic

Nonlimiting examples of red dopants include platinum(II) octaethylporphyrin (PtOEP), Ir(piq)$_3$, Btp$_2$Ir(acac), and DCJTB.

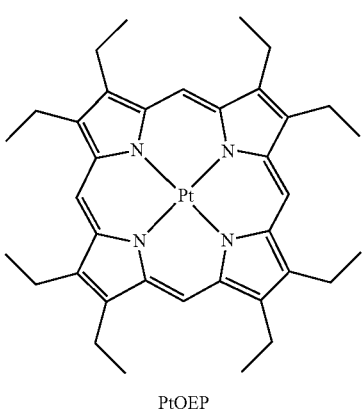

PtOEP

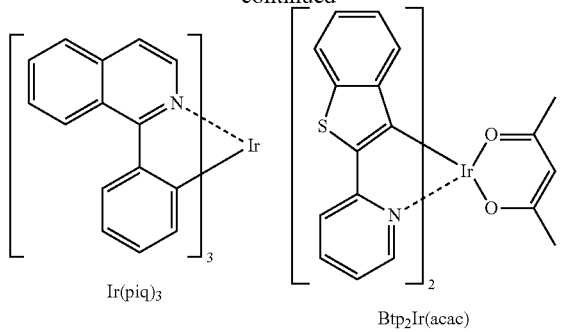

Ir(piq)$_3$

Btp$_2$Ir(acac)

Nonlimiting examples of green dopants include Ir(ppy)$_3$ (where "ppy" denotes phenylpyridine), Ir(ppy)$_2$(acac), Ir(mpyp)$_3$, and C545T

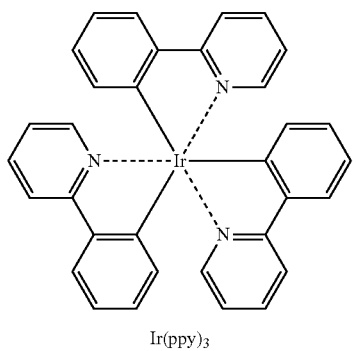

Ir(ppy)$_3$

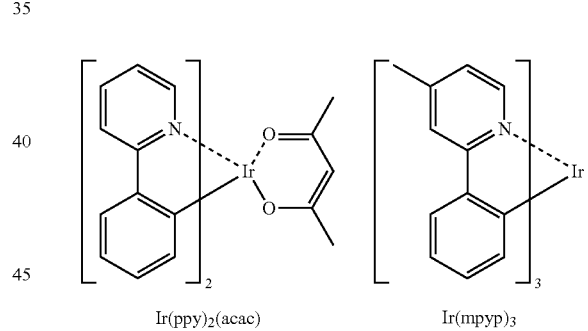

Ir(ppy)$_2$(acac)      Ir(mpyp)$_3$

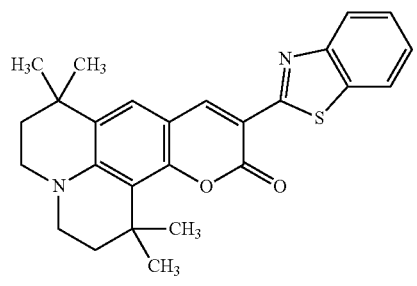

C545T

Nonlimiting examples of blue dopants include F$_2$Irpic, (F$_2$ppy)$_2$Ir(tmd), Ir(dfppz)$_3$, ter-fluorene, 4,4'-bis(4-diphenylaminostyryl)biphenyl (DPAVBi), and 2,5,8,11-tetra-t-butyl pherylene (TBPe).

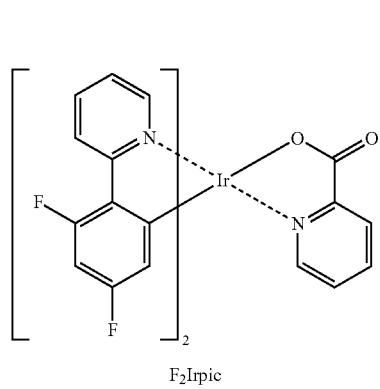
F₂Irpic

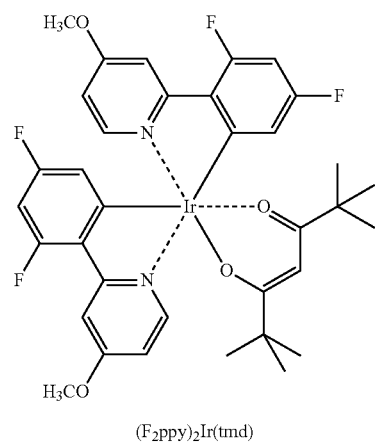
(F₂ppy)₂Ir(tmd)

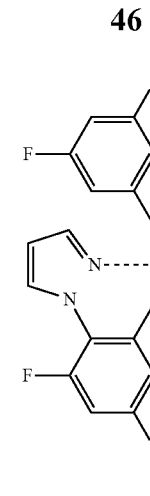
Ir(dfppz)₃

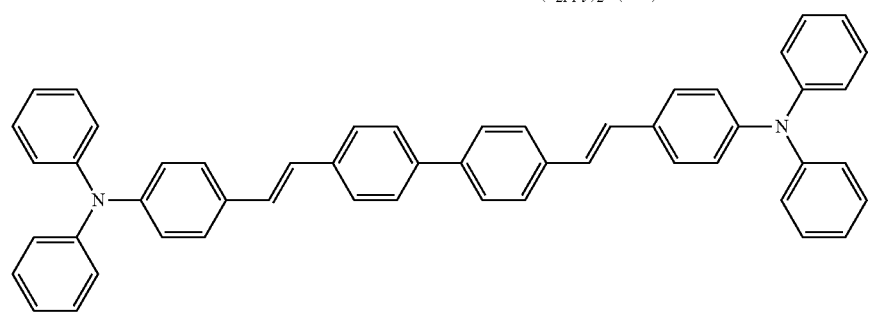
DPAVBi

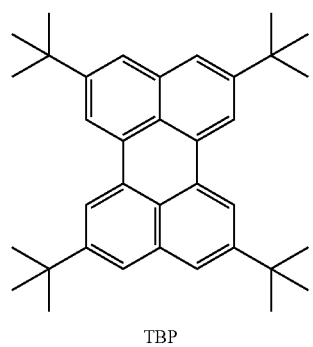
TBP

The amount of the dopant may be about 0.1 to about 20 parts by weight based on 100 parts by weight of the EML material, which is the total weight of the host and dopant. In some embodiments, for example, the amount of the dopant is about 0.5 to about 12 parts by weight based on 100 parts by weight of the EML material. When the amount of the dopant is within these ranges, concentration quenching may be substantially prevented.

The thickness of the EML may be about 100 to about 1000 Å. In some embodiments, for example, the thickness of the EML is about 200 to about 600 Å. When the thickness of the EML is within these ranges, good light emission characteristics may be obtained without increasing driving voltage.

When the EML includes a phosphorescent dopant, a hole blocking layer (HBL, not shown in FIG. 1) may be formed on the EML in order to prevent diffusion of triplet excitons or holes into the ETL. The HBL may be formed of any suitable material without limitation. Nonlimiting examples of suitable materials for the HBL include oxadiazole derivatives, triazole derivatives, phenanthroline derivatives, bis(2-methyl-8-quinolato)-(p-phenylphenolato)-aluminum (Balq), bathocuproine (BCP), and tris(N-arylbenzimidazole) (TPBI).

The thickness of the HBL may be about 50 to about 1000 Å. In some embodiments, for example, the thickness of the HBL is about 100 to about 300 Å. When the thickness of the HBL is within these ranges, good hole-blocking characteristics may be obtained without increasing driving voltage.

The ETL may be formed on the HBL or EML by vacuum deposition, spin coating, or casting. When the ETL is formed by vacuum deposition or spin coating, the deposition and coating conditions may be similar to those for formation of the HIL, although the deposition and coating conditions may vary according to the compound used to form the ETL.

The ETL may be formed of the heterocyclic compound of Formula 1 or any other ETL materials without limitation. Nonlimiting examples of ETL materials include quinoline derivatives, for example, tris(8-quinolinorate)aluminum (Alq₃), TAZ, and Balq.

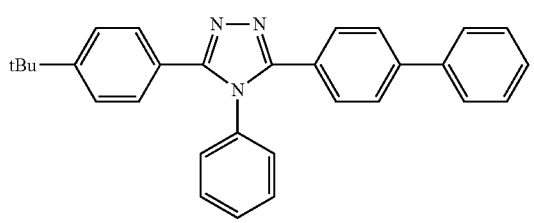

TAZ

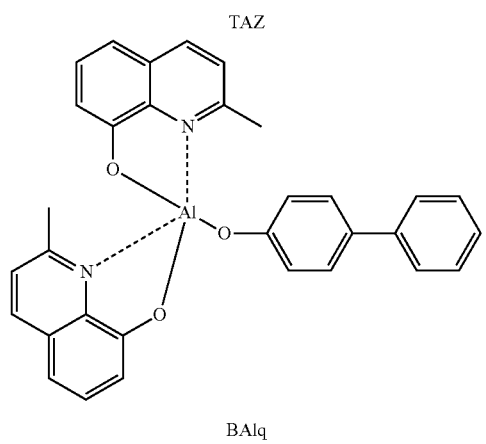

BAlq

The thickness of the ETL may be about 100 to about 1000 Å. In some embodiments, for example, the thickness of the ETL is about 100 to about 500 Å. When the ETL has a thickness within these ranges, the ETL may have good electron transport characteristics without substantially increasing driving voltage.

In addition, an electron injection layer (EIL) for facilitating the injection of electrons from the cathode may be formed on the ETL. The EIL may be formed of the heterocyclic compound of Formula 1. Alternatively, the EIL may be formed of any suitable electron transport layer material. Nonlimiting examples of electron transport layer materials include $BaF_2$, LiF, NaCl, CsF, $Li_2O$, BaO, and Liq.

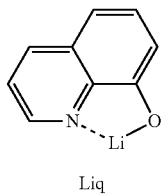

Liq

The deposition or coating conditions used to form the EIL may be similar to those used to form the HIL, although the deposition and coating conditions may vary according to the material used to form the EIL.

The thickness of the EIL may be about 1 to about 100 Å. In some embodiments, for example, the thickness of the EIL is about 5 to about 90 Å. When the EIL has a thickness within these ranges, the EIL may have good electron injection characteristics without substantially increasing driving voltage.

Finally, the second electrode may be formed on the EIL by vacuum deposition or sputtering. The second electrode may be a cathode or an anode. The material for forming the second electrode may be selected from metals, alloys, electrically conductive compounds, materials which have a low work function, and mixtures thereof. Nonlimiting examples of materials for the second electrode include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used as the second electrode.

The organic light-emitting device according to embodiments of the present invention may be included in various types of flat panel display devices, such as in passive matrix organic light-emitting display devices or active matrix organic light-emitting display devices. When the organic light-emitting device is included in an active matrix organic light-emitting display device including a thin-film transistor, the first electrode on the substrate may function as a pixel electrode, and be electrically connected to a source electrode or a drain electrode of the thin-film transistor. Moreover, the organic light-emitting device may also be included in a flat panel display device having a double-sided screen.

According to embodiments of the present invention, at least one layer of the organic light-emitting device may be formed of the heterocyclic compound of Formula 1 and can be formed using a deposition method or a wet method of coating a solution of the heterocyclic compound of Formula 1.

The following examples are presented for illustrative purposes only, and do not limit the scope of the present invention.

Synthesis Example 1

Synthesis of Compound 5

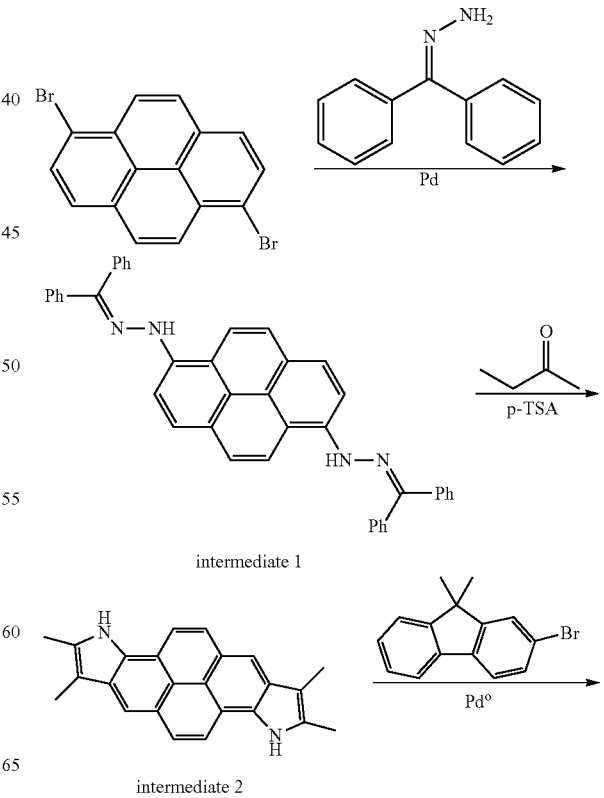

-continued

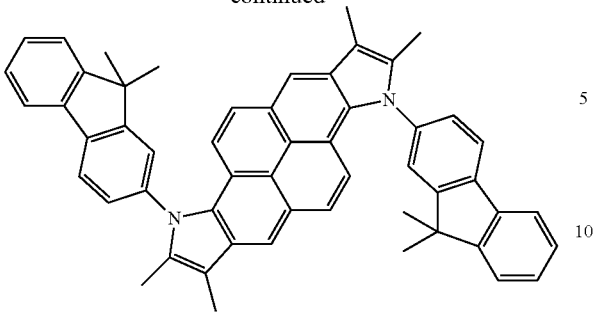

5

Synthesis of Intermediate 1

3.6 g (10 mmol) of 1,6-dibromopyrene, 2.15 g (11 mmol) of benzophenone hydrazone, 1.44 g (15 mmol) of t-BuONa, 45 mg (0.2 mmol) of Pd(OAc)$_2$, and 95 mg (0.2 mmol) of 2-dicyclohexylphosphino-2',4',6'-triisopropylbiphenyl were dissolved in 30 mL of toluene and stirred at 90° C. for 3 hours. The reaction product was cooled to room temperature. Distilled water was added thereto and the product was extracted twice with 80 mL of diethylether and once with 80 mL of dichloromethane. The organic layer was collected and dried using magnesium sulfate, followed by filtration. The solvent was evaporated, and the residue was separated and purified using silica gel column chromatography to obtain 5.5 g (yield 93%) of Intermediate 1. This compound was identified using high-resolution mass spectrometry (HR-MS). $C_{42}H_{30}N_4$ calc.: 590.2470; found: 590.2473.

Synthesis of Intermediate 2

50 mL of methylethylketone was added to a mixture including 5.9 g (10 mmol) of Intermediate 1 and 3.8 g (20 mmol) of p-toluenesulfonic acid monohydrate, and then the mixture was stirred at 110° C. for 24 hours. The reaction product was cooled to room temperature. Distilled water was added thereto and the product was extracted twice with 80 mL of diethylether and twice with 80 mL of dichloromethane. The organic layer was collected and dried using magnesium sulfate, followed by filtration. The solvent was evaporated, and the residue was separated and purified using silica gel column chromatography to obtain 2.4 g (yield 71%) of Intermediate 2. This compound was identified using HR-MS. $C_{24}H_{20}N_2$ calc.: 336.1626; found: 336.1628.

Synthesis of Compound 5

Under a nitrogen atmosphere, 2.35 g (7.0 mmol) of Intermediate 2, 2.29 g (8.4 mmol) of 2-bromo-9,9-dimethylfluorene, 2.01 g (21 mmol) of t-BuONa, 130 mg (0.14 mmol) of Pd$_2$(dba)$_3$, and 28 mg (0.14 mmol) of P(t-Bu)$_3$ were dissolved in 30 ml of toluene and stirred at 90° C. for 3 hours. After the reaction was completed, the reaction product was cooled to room temperature and extracted three times with distilled water and 50 ml of diethylether. The organic layer was collected and dried using magnesium sulfate to evaporate the solvent. The residue was separated and purified using silica gel column chromatography to obtain 3.5 g (yield 69%) of Compound 5. This compound was identified using HR-MS and nuclear magnetic resonance (NMR). $C_{54}H_{44}N_2$ calc.: 720.3504; found: 720.3509; $^1$H NMR (CDCl$_3$, 400 MHz) δ (ppm) 8.12 (d, 2H), 7.95 (d, 2H), 7.80 (d, 2H), 7.57 (d, 2H), 7.51 (d, 2H), 7.31 (d, 2H), 7.22 (t, 2H), 6.95 (t, 2H), 6.36 (d, 2H), 6.01 (dd, 2H), 2.29 (s, 6H), 2.22 (s, 6H), 1.85 (s, 12H).

Synthesis Example 2

Synthesis of Compound 8

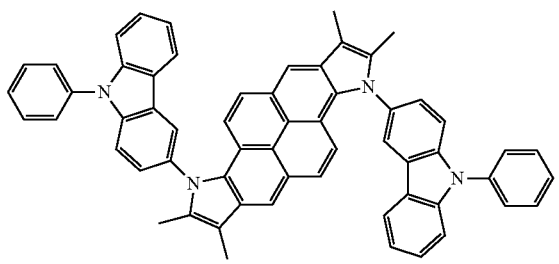

8

Compound 8 was synthesized with a yield of 72% in the same manner as Compound 5, except that 3-iodo-9-phenylcarbazole was used instead of 2-bromo-9,9-dimethylfluorene. This compound was identified using HR-MS and NMR. $C_{60}H_{42}N_4$ calc.: 818.3409; found: 818.3411; $^1$H NMR (CDCl$_3$, 400 MHz) δ (ppm) 8.13 (m, 4H), 8.05 (d, 2H), 7.95 (d, 2H), 7.48 (m, 10H), 7.32 (m, 10H), 6.63 (dd, 2H), 2.29 (s, 6H), 2.22 (s, 6H).

Synthesis Example 3

Synthesis of Compound 21

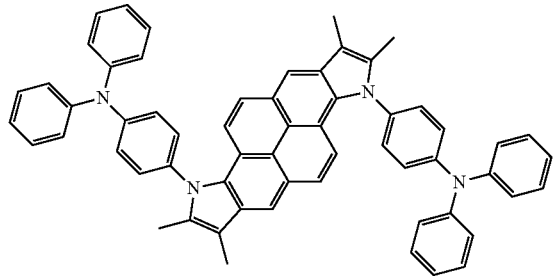

21

Compound 21 was synthesized with a yield of 78% in the same manner as Compound 5, except that 4-bromotriphenylamine was used instead of 2-bromo-9,9-dimethylfluorene. This compound was identified using HR-MS and NMR. $C_{60}H_{46}N_4$ calc.: 822.3722; found: 822.3725; $^1$H NMR (CDCl$_3$, 400 MHz) δ (ppm) 8.13 (d, 2H), 7.95 (d, 2H), 7.42 (d, 4H), 7.30 (m, 10H), 6.62 (t, 4H), 6.10 (d, 4H), 5.69 (d, 8H), 2.29 (s, 6H), 2.22 (s, 6H).

Synthesis Example 4

Synthesis of Compound 26

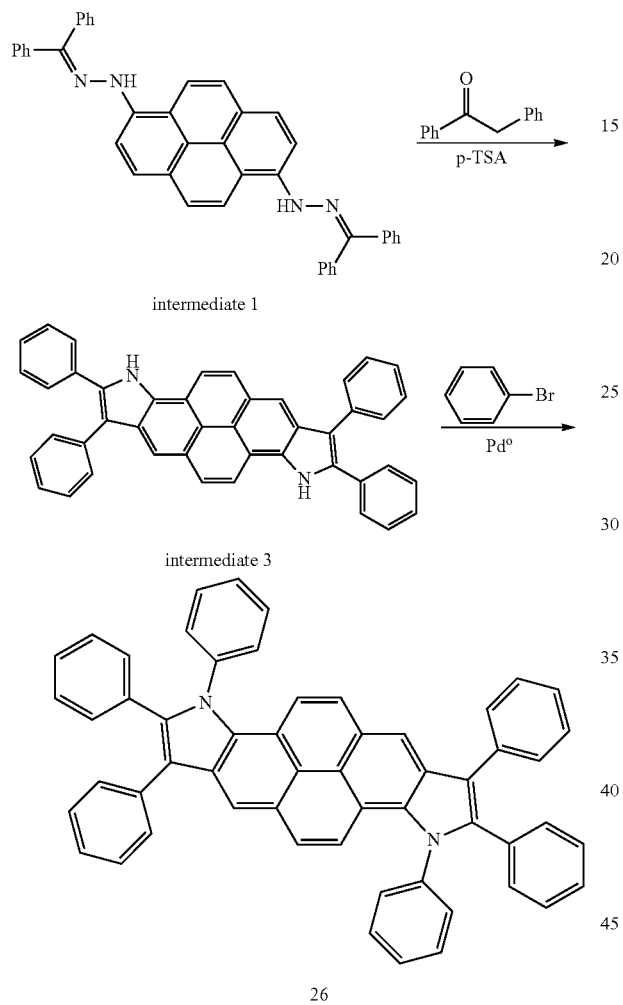

Synthesis of Intermediate 3

40 mL of ethanol and 20 mL of toluene were added to a mixture including 5.9 g (10 mmol) of Intermediate 1, 3.44 g (20 mmol) of p-toluenesulfonic acid monohydrate, and 3.92 g (20 mmol) of benzylphenylketone, and then the resultant mixture was stirred at 110° C. for 24 hours. The reaction product was cooled to room temperature. Distilled water was added thereto and the product was extracted twice with 60 mL of diethylether and twice with 60 mL of dichloromethane. The organic layer was collected and dried using magnesium sulfate, followed by filtration. The solvent was evaporated, and the residue was separated and purified using silica gel column chromatography to obtain 7.92 g (yield 66%) of Intermediate 3. This compound was identified using HR-MS. C$_{60}$H$_{46}$N$_4$ calc.: 822.3722; found: 822.3725.

Synthesis of Compound 26

Compound 26 was synthesized with a yield of 82% in the same manner as Compound 5, except that Intermediate 3 (instead of Intermediate 2) was reacted with the bromobenzene. This compound was identified using HR-MS and NMR. C$_{56}$H$_{36}$N$_2$ calc. 736.2878; found: 736.2880; $^1$H NMR (CDCl$_3$, 400 MHz) δ (ppm) 8.15 (d, 2H), 8.10 (d, 2H), 7.88 (s, 2H), 7.57-7.25 (m, 26H), 7.05 (d, 4H).

Synthesis Example 5

Synthesis of Compound 30

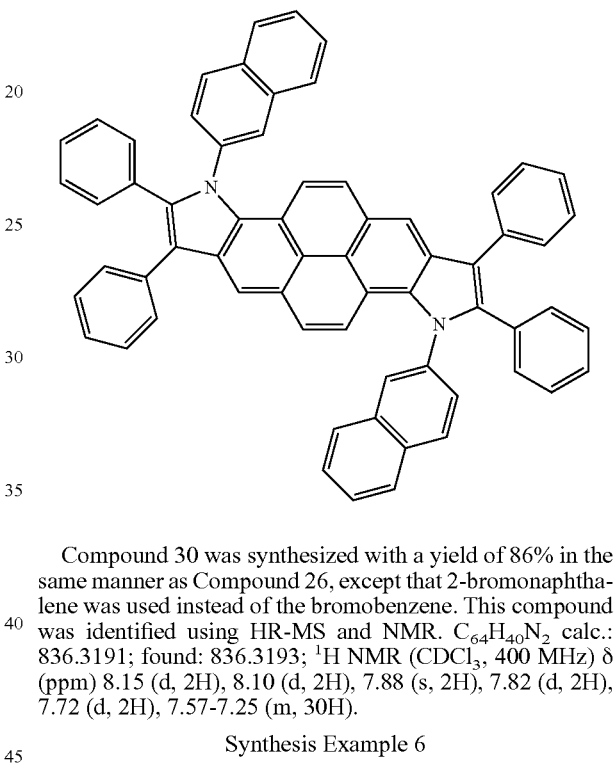

Compound 30 was synthesized with a yield of 86% in the same manner as Compound 26, except that 2-bromonaphthalene was used instead of the bromobenzene. This compound was identified using HR-MS and NMR. C$_{64}$H$_{40}$N$_2$ calc.: 836.3191; found: 836.3193; $^1$H NMR (CDCl$_3$, 400 MHz) δ (ppm) 8.15 (d, 2H), 8.10 (d, 2H), 7.88 (s, 2H), 7.82 (d, 2H), 7.72 (d, 2H), 7.57-7.25 (m, 30H).

Synthesis Example 6

Synthesis of Compound 47

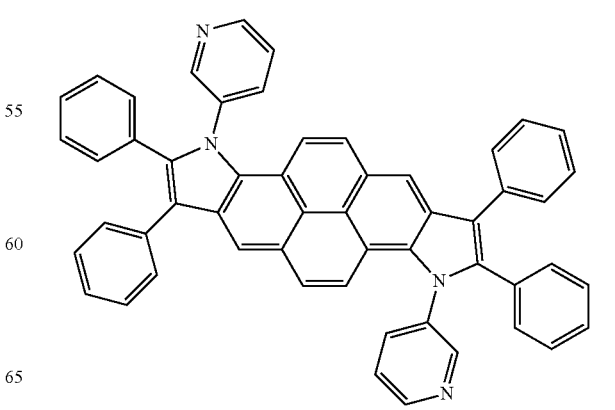

Compound 47 was synthesized with a yield of 76% in the same manner as Compound 26, except that 2-bromopyridine was used instead of bromobenzene. This compound was identified using HR-MS and NMR. $C_{54}H_{34}N_4$ calc.: 738.2783; found: 738.2788; $^1$H NMR (CDCl$_3$, 400 MHz) δ (ppm) 8.74 (m, 2H), 8.31 (m, 2H), 8.19 (d, 2H), 8.14 (d, 2H), 7.972 (s, 2H), 7.57-7.24 (m, 22H), 7.08-7.05 (m, 2H).

Example 1

An anode was prepared by cutting a Corning 15 Ωcm$^2$ (1200 Å) ITO glass substrate to a size of 50 mm×50 mm×0.7 mm, ultrasonically cleaning the glass substrate using isopropyl alcohol and pure water for 5 minutes each, and then irradiating with UV light for 30 minutes and exposing to ozone to clean. Then, the anode was mounted in a vacuum deposition apparatus.

2-TNATA was vacuum-deposited on the anode to form a hole injection layer having a thickness of 600 Å, and 4,4'-bis[N-(1-naphthyl)-N-phenylamino]biphenyl (NPB) was vacuum-deposited on the hole injection layer to form a hole transport layer having a thickness of 300 Å.

9,10-di-naphthalene-2-yl-anthracene (DNA) as a blue fluorescent host and Compound 5 as a fluorescent dopant were co-deposited at a weight ratio of 98:2 on the hole transport layer to form an emission layer having a thickness of 300 Å.

Next, Alq$_3$ was deposited on the emission layer to form an electron transport layer having a thickness of 300 Å, and LiF was deposited on the electron transport layer to form an electron injection layer having a thickness of 10 Å. Finally, Al was vacuum-deposited on the electron injection layer to a thickness of 3000 Å to form a LiF/Al electrode (cathode), thereby completing the manufacture of an organic light-emitting device.

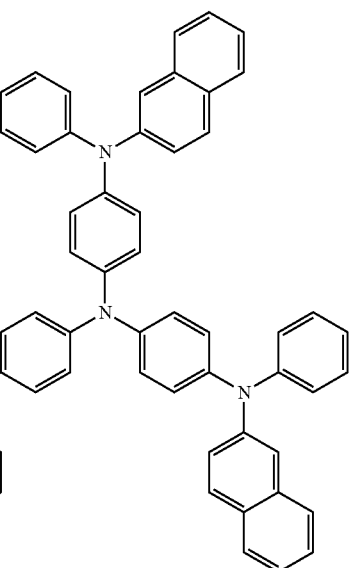

2-TNATA

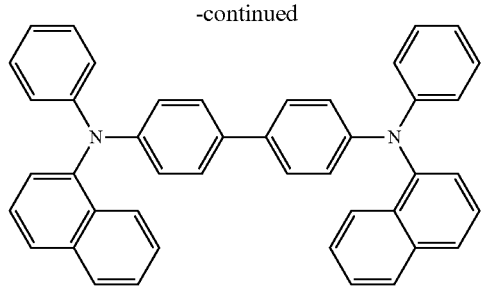

NPB

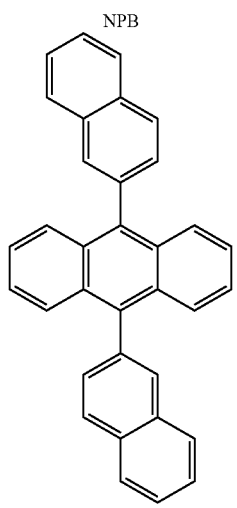

DNA

Example 2

An organic light-emitting device was manufactured in the same manner as Example 1, except that Compound 8 was used instead of Compound 5 to form the emission layer.

Example 3

An organic light-emitting device was manufactured in the same manner as Example 1, except that Compound 21 was used instead of Compound 5 to form the emission layer.

Example 4

An organic light-emitting device was manufactured in the same manner as Example 1, except that Compound 26 was used instead of Compound 5 to form the emission layer.

Example 5

An organic light-emitting device was manufactured in the same manner as Example 1, except that Compound 30 was used instead of Compound 5 to form the emission layer.

Example 6

An organic light-emitting device was manufactured in the same manner as Example 1, except that Compound 47 was used instead of Compound 5 to form the emission layer.

Comparative Example 1

An organic light-emitting device was manufactured in the same manner as Example 1, except that 1,4-bis-(2,2-diphenylvinyl)biphenyl (DPVBi) was used instead of Compound 5 to form the emission layer.

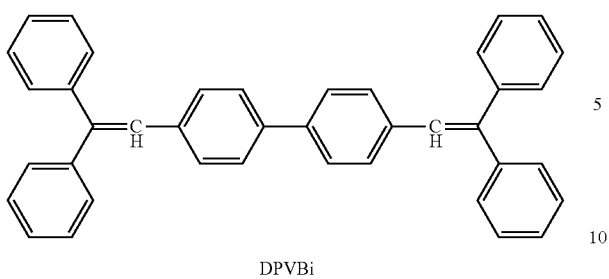

DPVBi

The driving voltage, luminance, color coordinates, and luminescent efficiency of each of the organic light-emitting devices manufactured according to Examples 1 through 6 and Comparative Example 1 were measured at a current density of 50 mA/cm². The half-life span of each of the organic light-emitting devices manufactured according to Examples 1 through 6 and Comparative Example 1 were measured at a current density of 100 mA/cm². The results are shown in Table 1 below.

TABLE 1

|  | Light-emitting material | Driving voltage (V) | Current density (mA/cm²) | Luminance (cd/m²) | Luminescent efficiency (cd/A) | Emission color | Half life-span (hr @ 100 mA/cm²) |
|---|---|---|---|---|---|---|---|
| Example 1 | Compound 5 | 6.57 | 50 | 2,350 | 4.7 | blue | 240 hr |
| Example 2 | Compound 8 | 6.76 | 50 | 2,654 | 5.31 | blue | 256 hr |
| Example 3 | Compound 21 | 6.54 | 50 | 3,110 | 6.22 | turquoise blue | 198 hr |
| Example 4 | Compound 26 | 6.42 | 50 | 2,963 | 5.93 | blue | 258 hr |
| Example 5 | Compound 30 | 6.62 | 50 | 3.256 | 6.51 | blue | 236 hr |
| Example 6 | Compound 47 | 6.21 | 50 | 1,835 | 3.67 | blue | 157 hr |
| Comparative Example 1 | DPVBi | 7.85 | 50 | 1,560 | 3.12 | blue | 113 hr |

Referring to Table 1, the organic light-emitting devices including the heterocyclic compounds of Formula 1 according to embodiments of the present invention had better driving voltage characteristics than the device including DPVBi. Thus, the devices including the heterocyclic compounds of Formula 1 had higher luminescent efficiency and good I-V-L characteristics. In particular, lifetime characteristics were markedly improved in the organic light-emitting devices according to Examples 1 through 6, as compared to the organic light-emitting device according to Comparative Example 1.

The heterocyclic compounds of Formula 1 have high Tgs or high melting points, and thus have high heat resistance against Joule's heat generated between an organic layer and a metallic electrode when light emission occurs. The heterocyclic compounds of Formula 1 also have high durability in high-temperature environments, good electrical characteristics, and high charge transporting capabilities. Thus, the heterocyclic compounds of Formula 1 may be used as at least one of an electron injecting material, an electron transporting material, and a material for emission layers, where these materials are suitable for any color fluorescent and phosphorescent devices, such as red, green, blue, and white fluorescent and phosphorescent devices.

Organic light-emitting devices including organic layers containing the heterocyclic compounds of Formula 1 have high durability when stored or operated, and have high efficiency, low driving voltages, and high luminance.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heterocyclic compound comprising a compound represented by Formula 1:

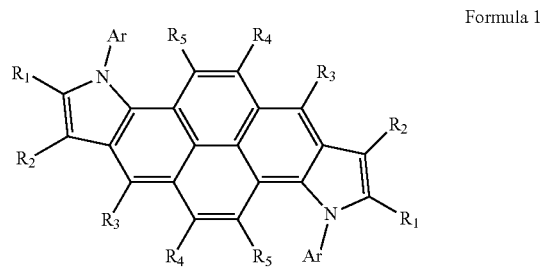

Formula 1 wherein:

Ar is selected from the group consisting of substituted and unsubstituted $C_6$-$C_{60}$ aryl groups, substituted and unsubstituted $C_4$-$C_{60}$ heteroaryl groups, amino groups substituted with at least one selected from the group consisting of substituted and unsubstituted $C_6$-$C_{50}$ aryl groups, and substituted and unsubstituted $C_6$-$C_{60}$ condensed polycyclic groups; and each of $R_3$ through $R_5$ is independently selected from the group consisting of hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_2$-$C_{50}$ alkoxycarbonyl groups, substituted and unsubstituted $C_6$-$C_{60}$ aryl groups, substituted and unsubstituted $C_6$-$C_{50}$ aryloxy groups, substituted and unsubstituted $C_6$-$C_{50}$ arylthio groups, amino groups substituted with at least one substituted or unsubstituted $C_6$-$C_{50}$ aryl groups, substituted and unsubstituted $C_3$-$C_{50}$ carbocyclic groups, substituted and unsubstituted $C_4$-$C_{60}$ heteroaryl groups, substituted and unsubstituted $C_4$-$C_{60}$ heterocyclic groups, substituted and unsubstituted $C_6$-$C_{60}$ condensed polycyclic groups, halogen atoms, cyano groups, hydroxyl groups, and carboxyl groups; and each of $R_1$ and $R_2$ is independently selected from the group consisting of:
  methyl groups;
  unsubstituted monocyclic to tricyclic aryl groups selected from the group consisting of phenyl groups, naphthyl groups, biphenyl groups, terphenyl groups, fluorenyl groups, and carbazolyl groups; and monocyclic to tricyclic aryl groups substituted with one to three substituents selected from the group consisting of $C_1$-$C_5$ alkyl groups, $C_1$-$C_5$ alkoxy groups, cyano groups, $C_1$-$C_5$ alkyl phenoxy groups, phenyl groups, halogen atoms, and —N(R')(R") groups wherein each of R' and R" is independently selected from the group consisting of hydrogen atoms, $C_1$-$C_{20}$ alkyl groups, $C_6$-$C_{20}$ aryl groups, and $C_3$-$C_{20}$ heteroaryl groups.

2. The heterocyclic compound of claim 1, wherein Ar is selected from the group consisting of:
unsubstituted monocyclic to tricyclic aryl groups selected from the group consisting of phenyl groups, naphthyl groups, biphenyl groups, terphenyl groups, fluorenyl groups, and carbazolyl groups; and
monocyclic to tricyclic aryl groups substituted with one to three substituents selected from the group consisting of $C_1$-$C_5$ alkyl groups, $C_1$-$C_5$ alkoxy groups, cyano groups, amino groups, phenoxy groups, phenyl groups, and halogen atoms.

3. The heterocyclic compound of claim 1, wherein the compound of Formula 1 is selected from the group consisting of compounds represented by Formulae 2 through 4:

Formula 2

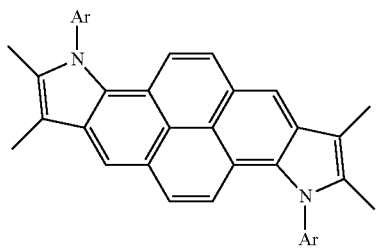

Formula 3

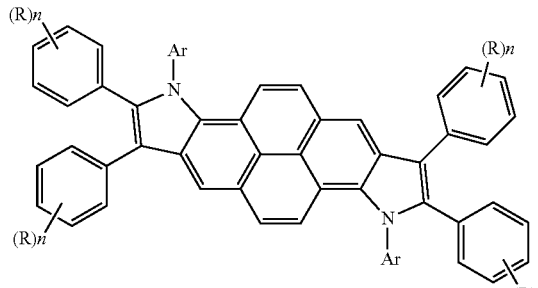

Formula 4

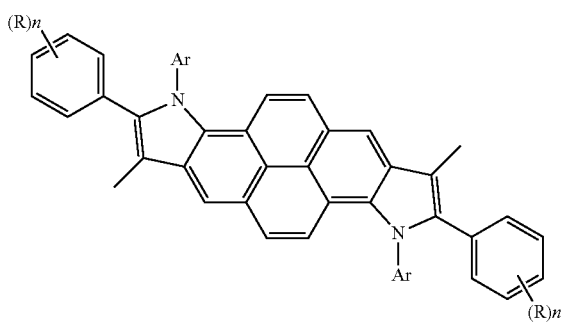

wherein:
Ar is selected from the group consisting of substituted and unsubstituted $C_6$-$C_{60}$ aryl groups, substituted and unsubstituted $C_4$-$C_{60}$ heteroaryl groups, amino groups substituted with at least one substituted or unsubstituted $C_6$-$C_{50}$ aryl groups, and substituted and unsubstituted $C_6$-$C_{60}$ condensed polycyclic groups;

R is selected from the group consisting of hydrogen atoms, $C_1$-$C_5$ alkyl groups, $C_1$-$C_5$ alkoxy groups, phenyl groups, and —N(R')(R") groups wherein at least one of R' and R" is selected from the group consisting of hydrogen atoms, $C_1$-$C_{20}$ alkyl groups, $C_6$-$C_{20}$ aryl groups, and $C_3$-$C_{20}$ heteroaryl groups; and n is an integer from 1 to 3.

4. The heterocyclic compound of claim 3, wherein Ar is selected from the group consisting of:
monocyclic to tricyclic aryl groups selected from the group consisting of phenyl groups, naphthyl groups, biphenyl groups, terphenyl groups, fluorenyl groups, and carbazolyl groups, and
monocyclic to tricyclic aryl groups selected from the group consisting of $C_6$-$C_{60}$ aryl groups, $C_4$-$C_{60}$ heteroaryl groups, amino groups substituted with at least one substituted or unsubstituted $C_6$-$C_{50}$ aryl group, and $C_6$-$C_{60}$ condensed polycyclic groups substituted with one to three substituents selected from the group consisting of $C_1$-$C_5$ alkyl groups, $C_1$-$C_5$ alkoxy groups, cyano groups, amino groups, phenoxy groups, phenyl groups, and halogen atoms.

5. The heterocyclic compound of claim 3, wherein Ar is selected from the group consisting of:

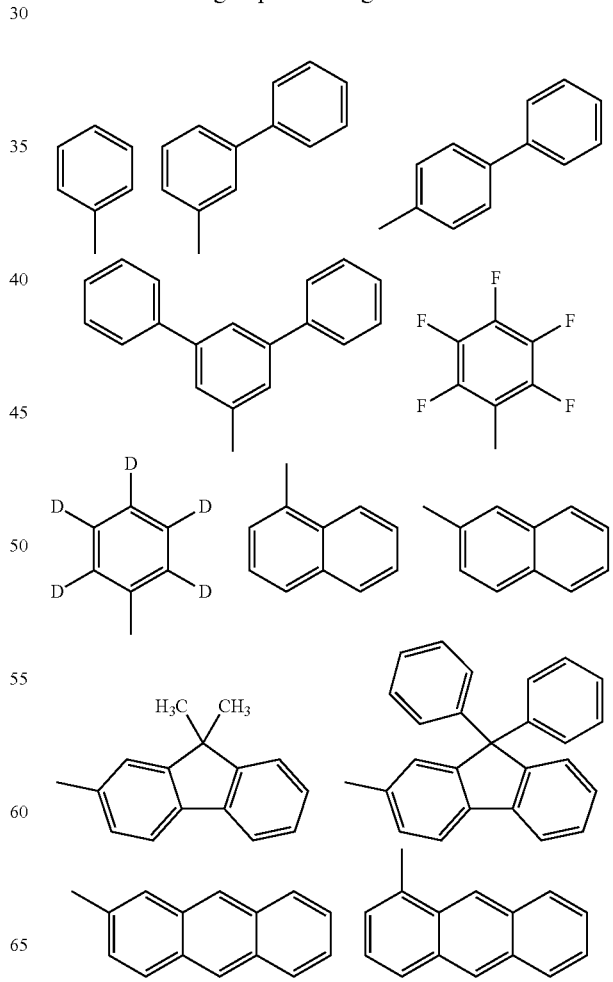

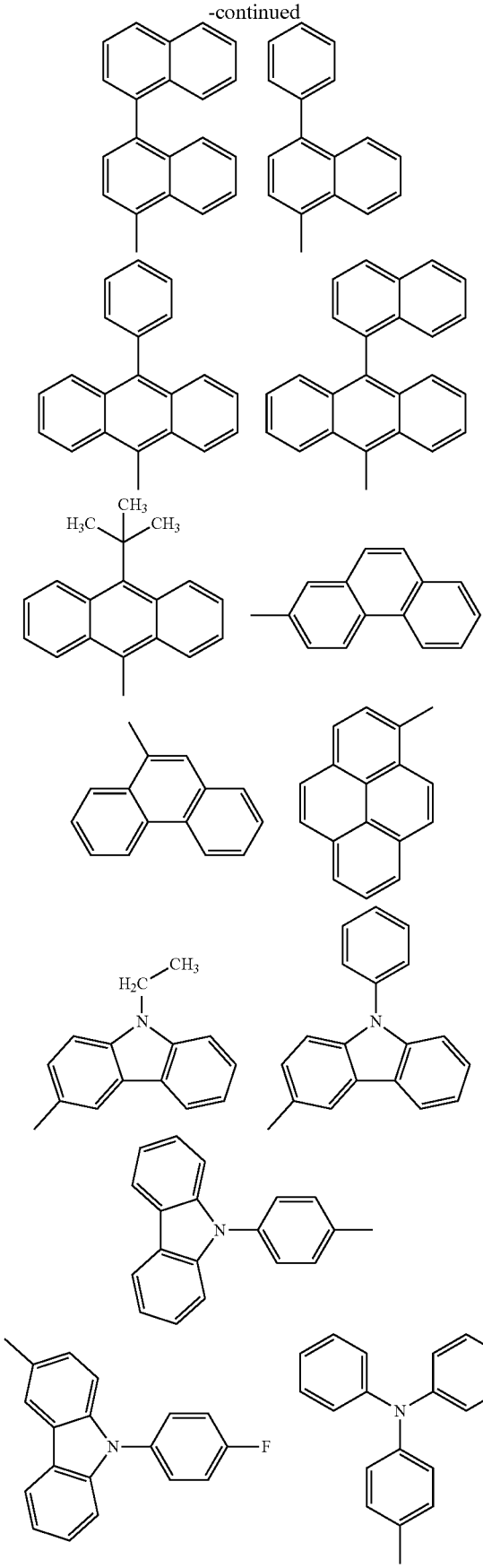
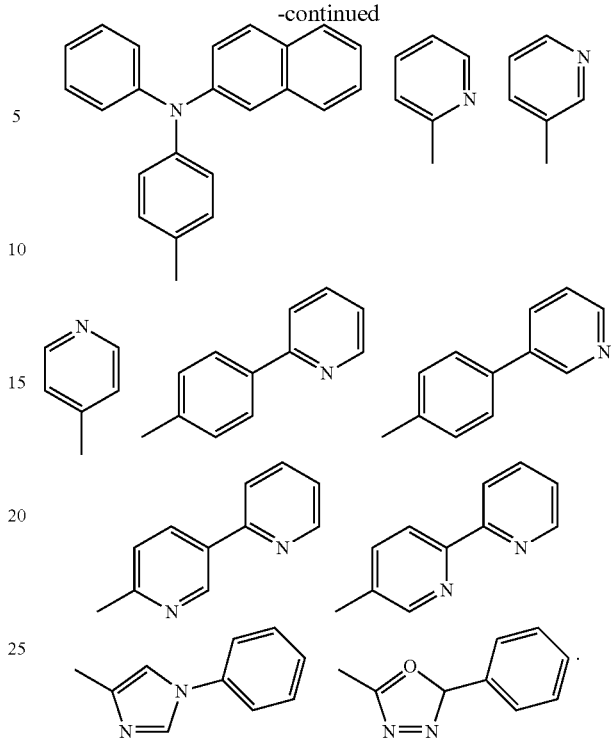
6. The heterocyclic compound of claim 3, wherein
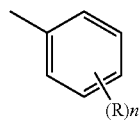
is a phenyl group, a naphthyl group, or an anthracenyl group.
7. The heterocyclic compound of claim 1, wherein the compound represented by Formula 1 is selected from the group consisting of Compounds 5, 8, 21, 26, 30 and 47:
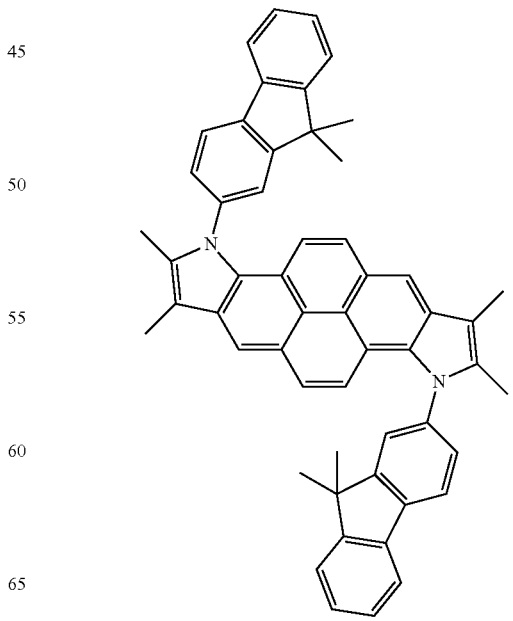

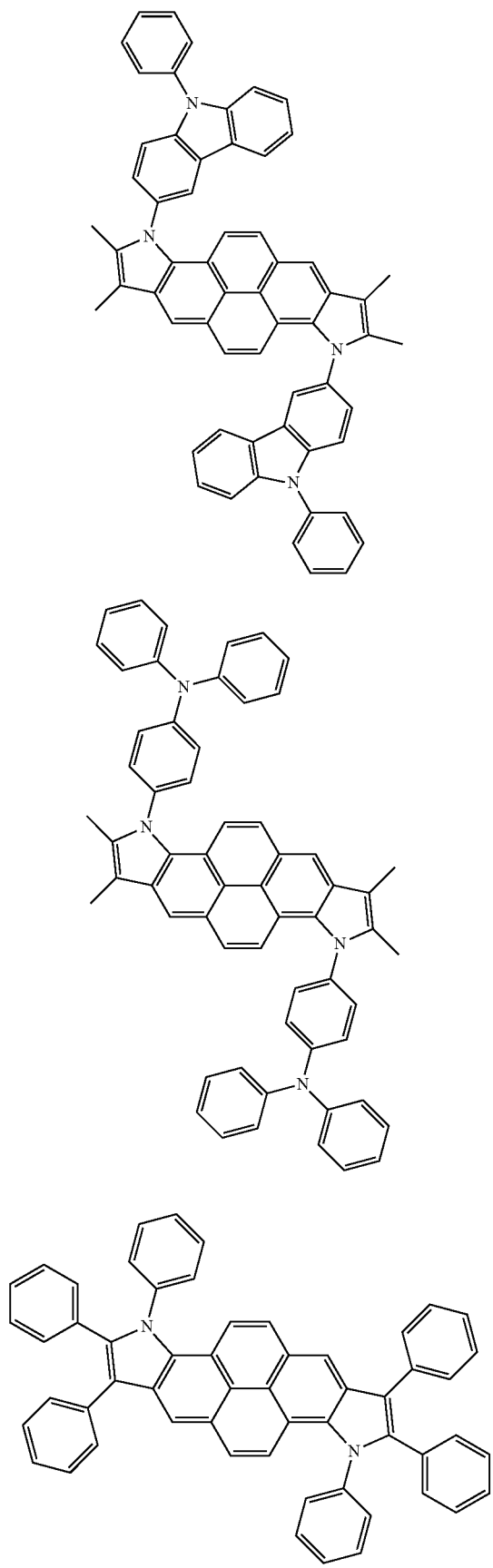
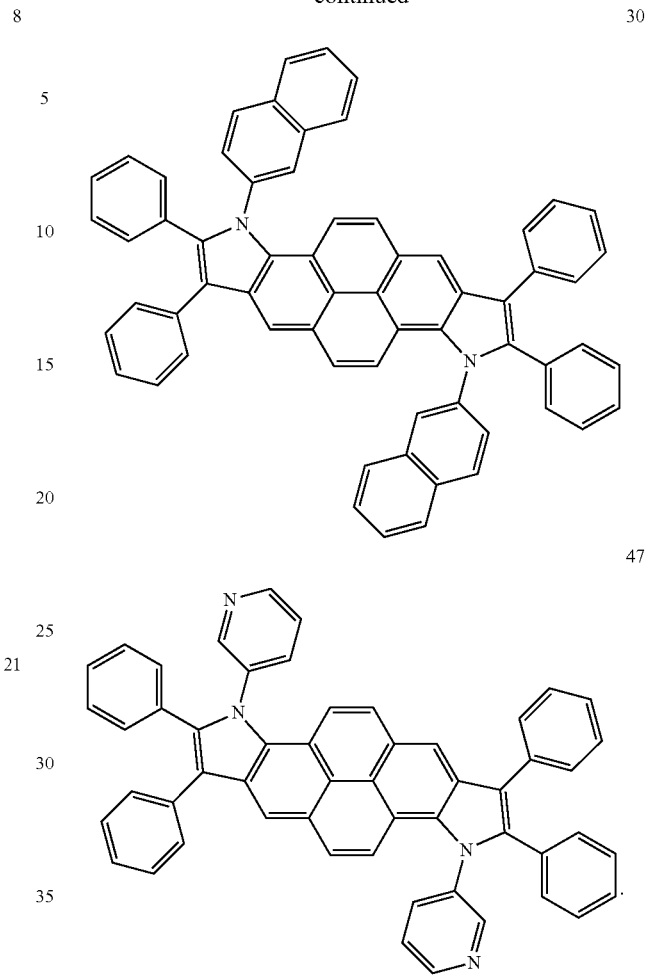

8. An organic light-emitting device comprising a first electrode, a second electrode, and an organic layer between the first electrode and the second electrode, wherein the organic layer comprises at least one organic layer comprising the heterocyclic compound represented by Formula 1 of claim 1.

9. The organic light-emitting device of claim 8, wherein the at least one organic layer comprises an electron injection layer or an electron transport layer.

10. The organic light-emitting device of claim 8, wherein the at least one organic layer comprises an emission layer or a single layer having electron injecting capability and electron transporting capability.

11. The organic light-emitting device of claim 8, wherein the at least one organic layer comprises an emission layer comprising the heterocyclic compound represented by Formula 1 as a host for a fluorescent or phosphorescent device.

12. The organic light-emitting device of claim 8, wherein the at least one organic layer comprises an emission layer, and an electron transport layer or an electron injection layer, wherein the electron transport layer or the electron injection layer comprises the heterocyclic compound represented by Formula 1, and the emission layer comprises an anthracene compound or a $C_4$-$C_{60}$ heteroaryl compound or a styryl compound.

13. The organic light-emitting device of claim 8, wherein the at least one organic layer comprises an emission layer and an electron transport layer or an electron injection layer, wherein the electron transport layer or the electron injection layer comprises the heterocyclic compound represented by Formula 1, and the emission layer comprises a red emission layer, a green emission layer, a blue emission layer, and a white emission layer, wherein at least one of the red emission layer, the green emission layer, the blue emission layer and the white emission layer comprises a phosphorescent compound.

14. The organic light-emitting device of claim 8, wherein the at least one organic layer comprises at least one layer selected from the group consisting of a hole injection layer, a hole transport layer, an electron blocking layer, an emission layer, a hole blocking layer, an electron transport layer, and an electron injection layer.

15. The organic light-emitting device of claim 14, wherein the organic light-emitting device has a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure.

16. A flat panel display device comprising the organic light-emitting device of claim 8, wherein the first electrode of the organic light-emitting device is electrically connected to a source electrode or a drain electrode of a thin film transistor.

17. An organic light-emitting device comprising a first electrode, a second electrode, and an organic layer between the first electrode and the second electrode, wherein the organic layer comprises at least one layer comprising the heterocyclic compound of claim 1, the at least one layer being formed using a wet process.

18. The heterocyclic compound of claim 1, wherein the compound represented by Formula 1 is selected from the group consisting of Compounds 1 through 54:

1
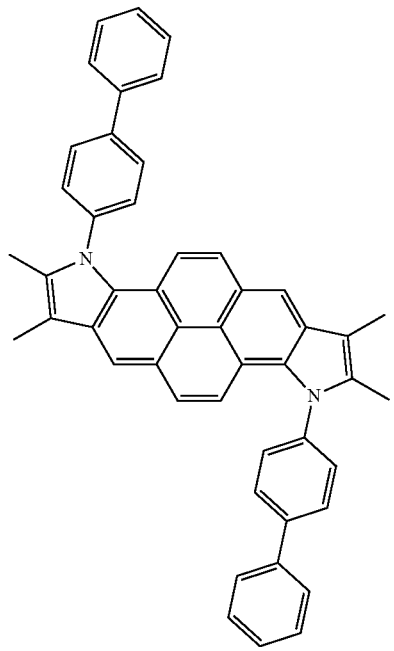

2
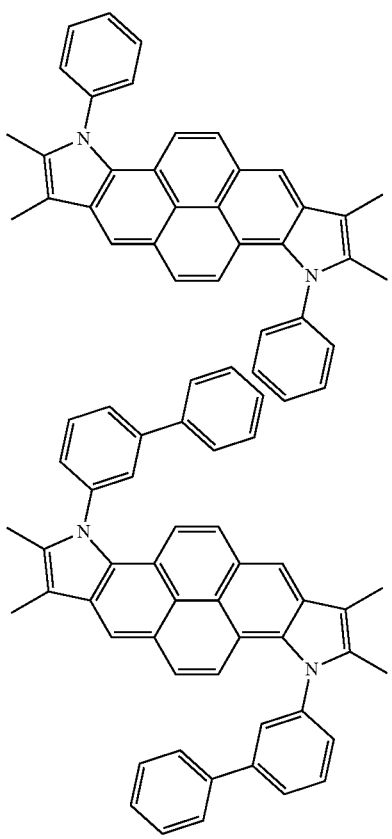

-continued

3
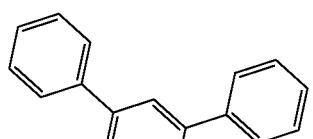

4
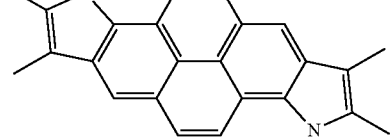
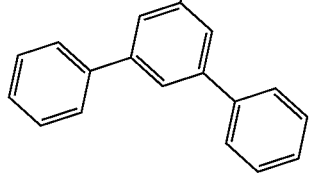

65
-continued
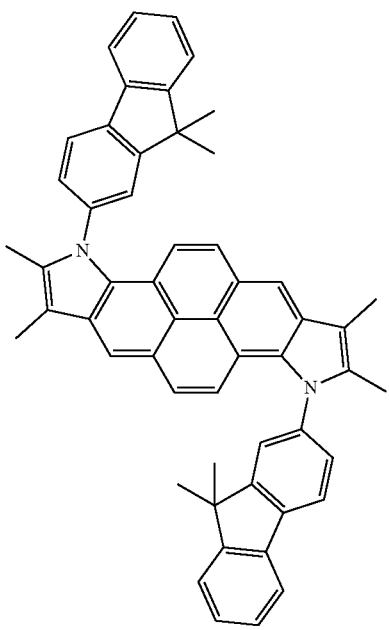
5
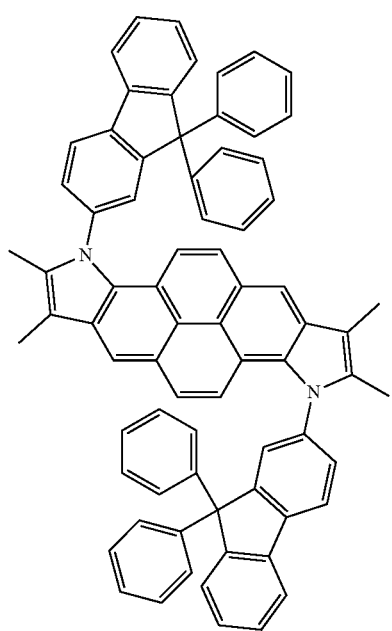
6
66
-continued
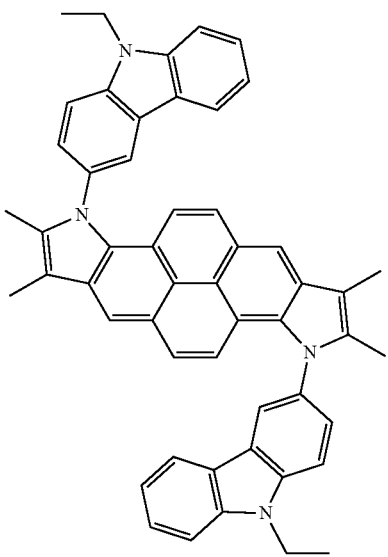
7
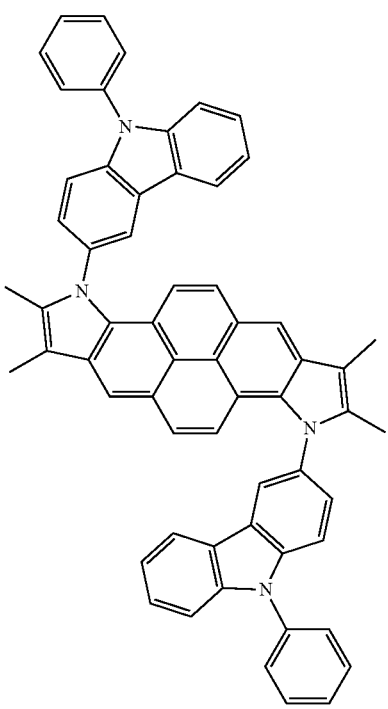
8

9
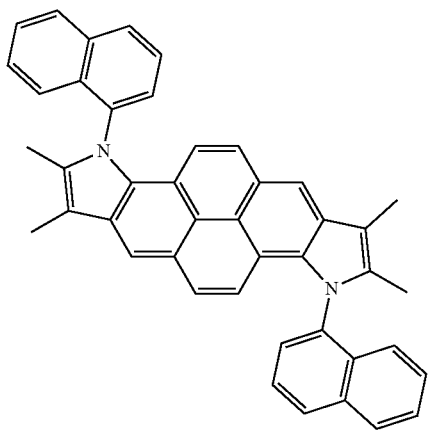
10
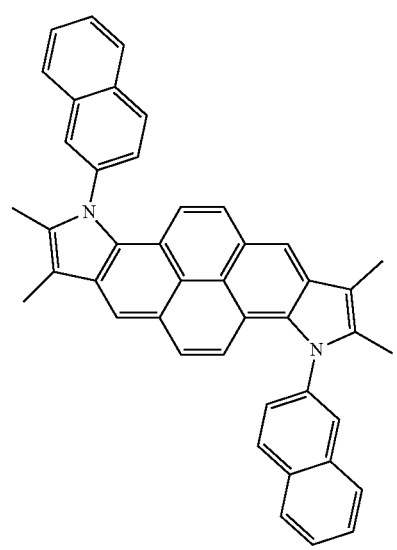
11
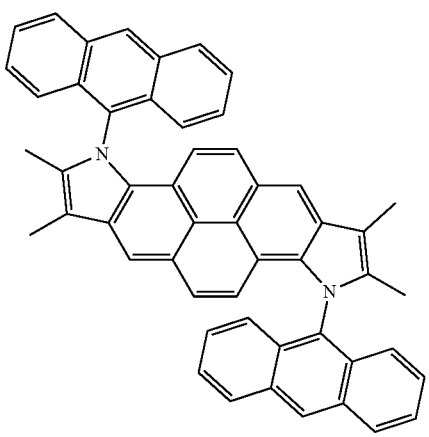
12
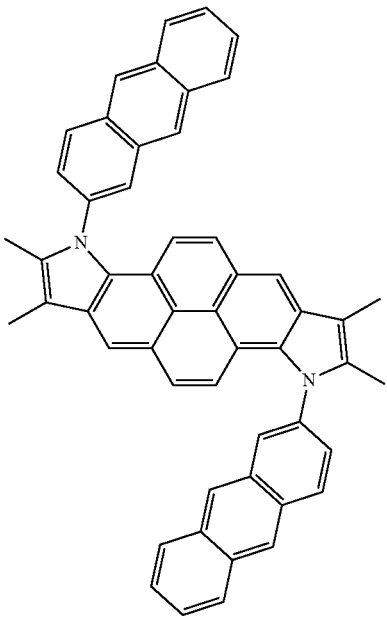
13
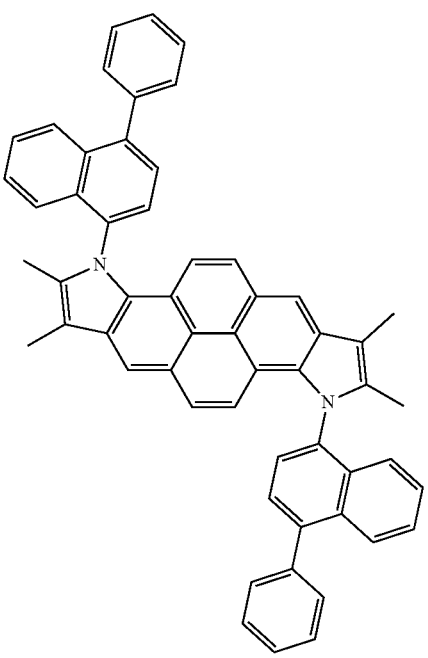

14
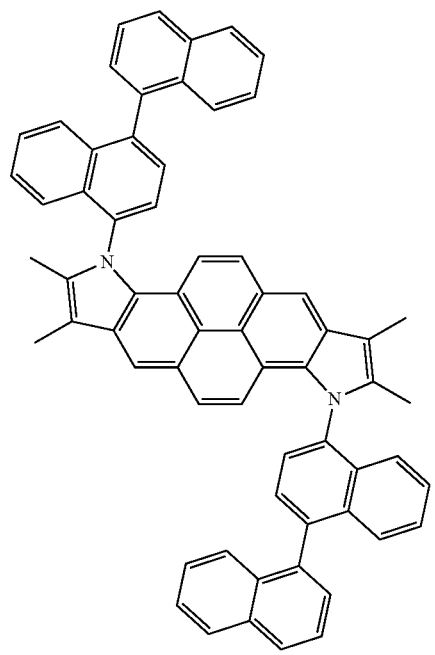
15
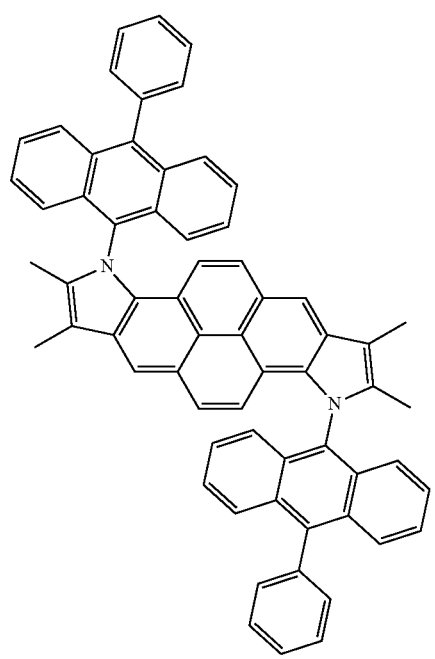
16
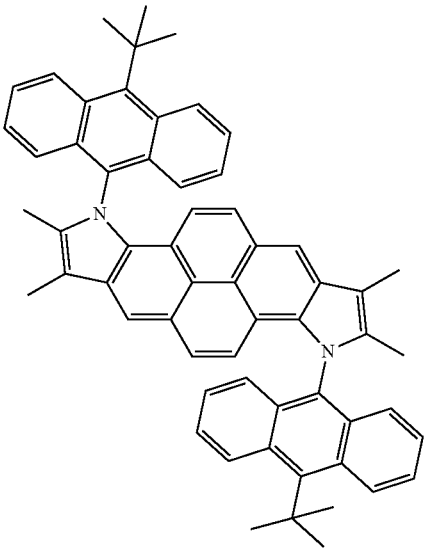
17
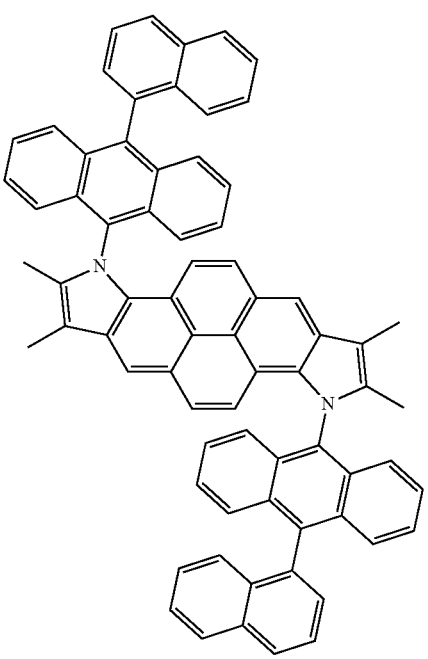

71
-continued
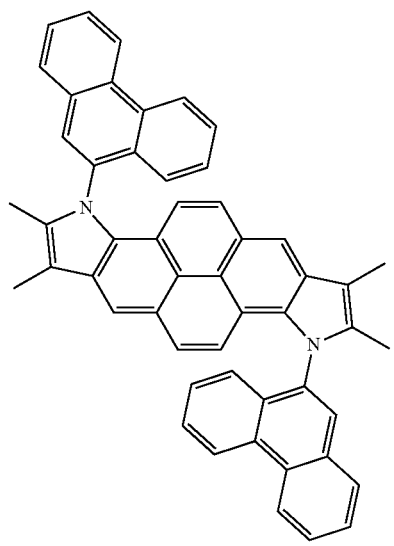
18
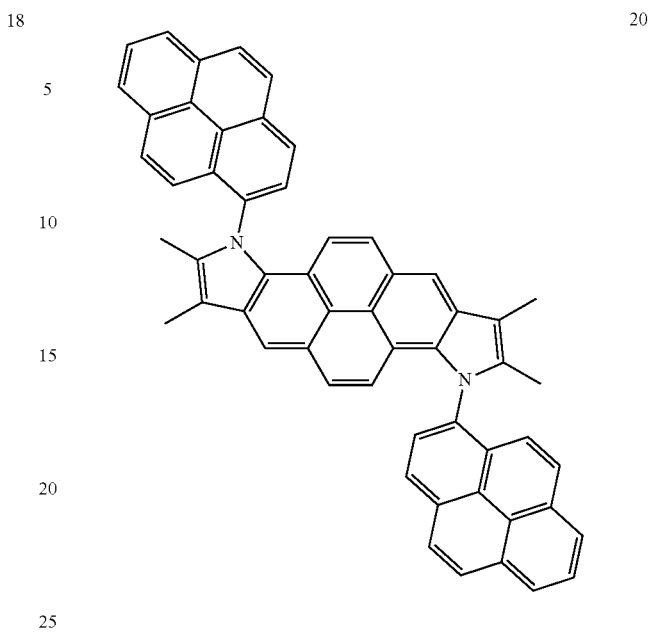
20
72
-continued
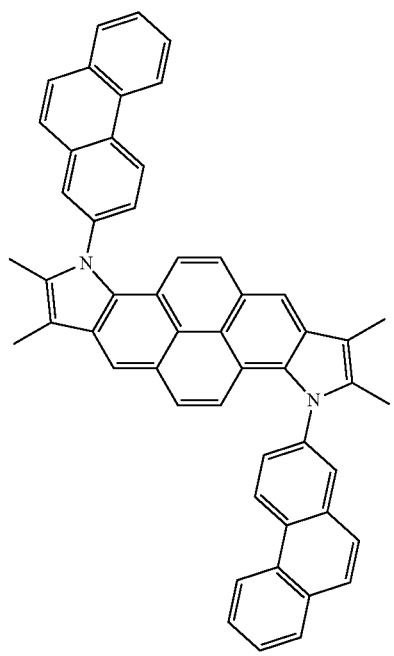
19
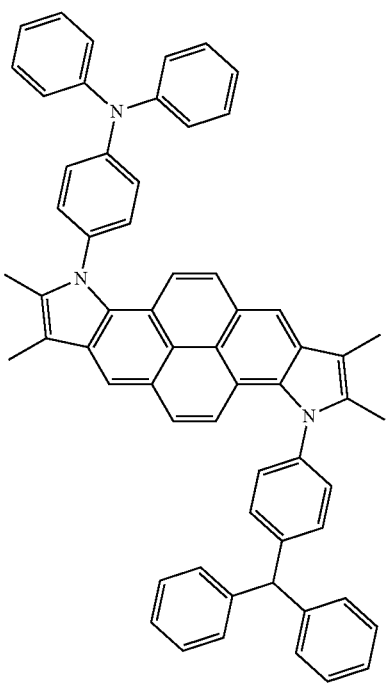
21

22
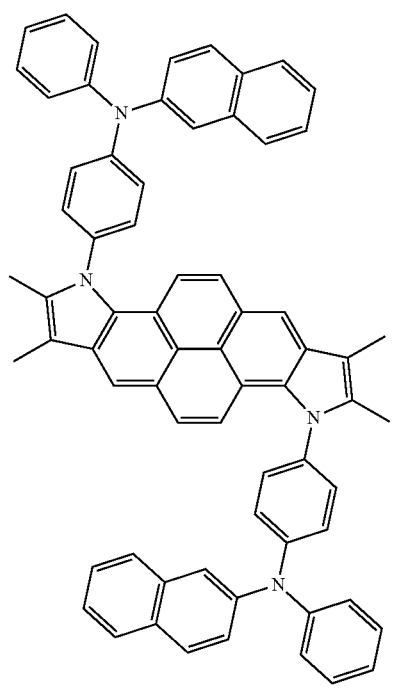
23
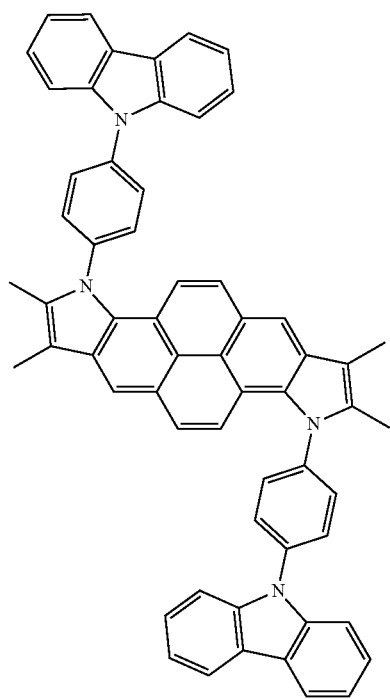
24
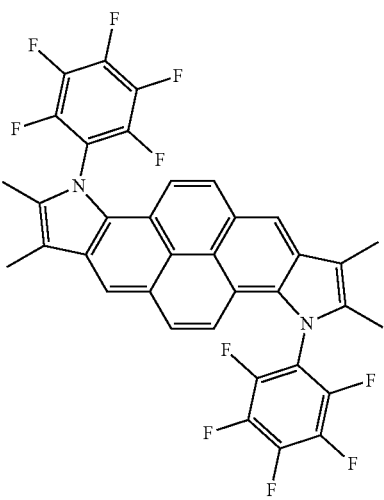
25
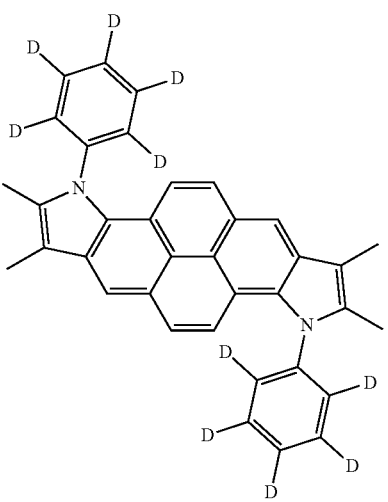
26
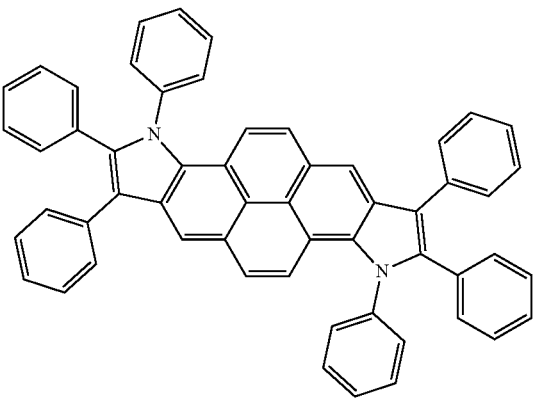

27
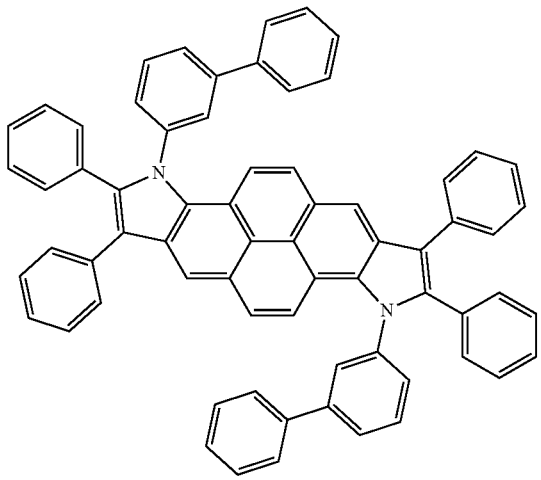
28
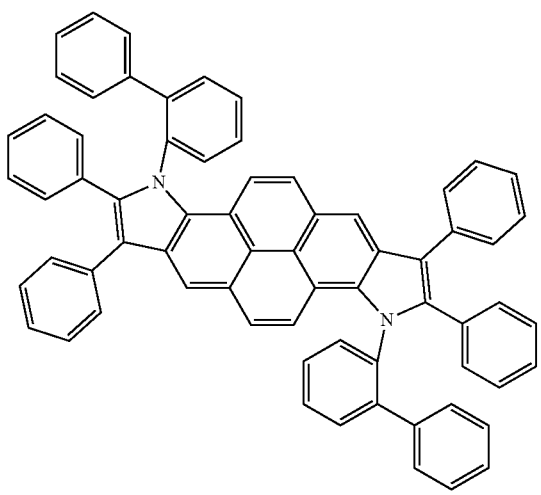
29
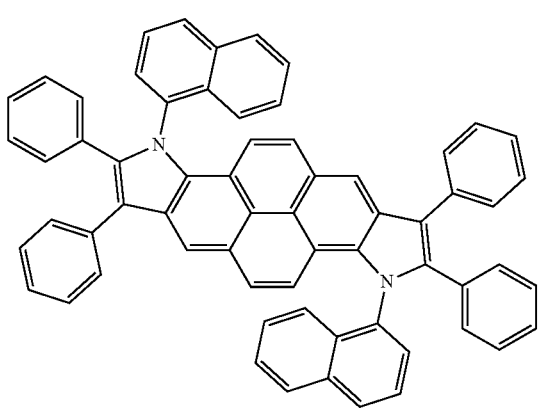
30
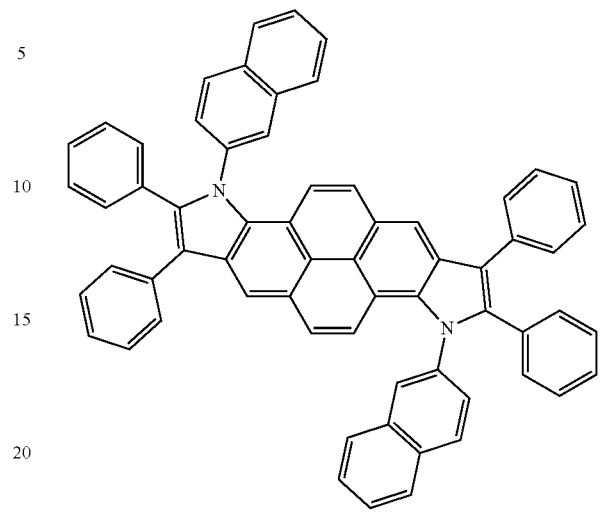
31
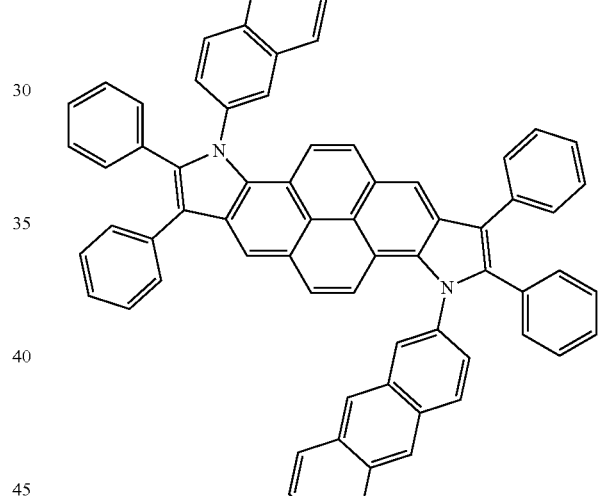
32
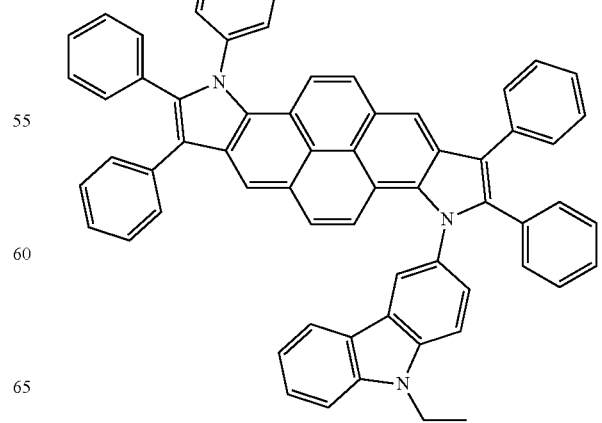

33
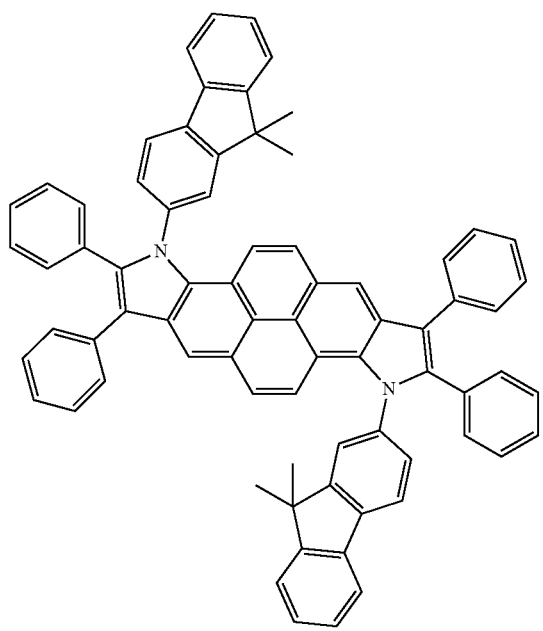
34
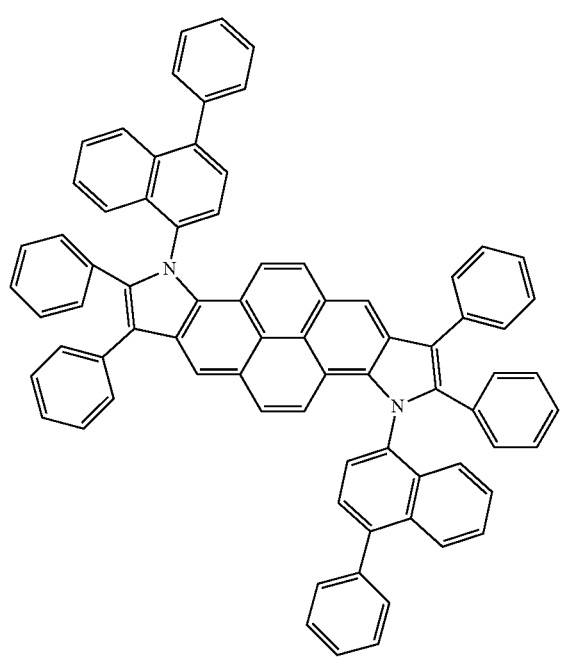
35
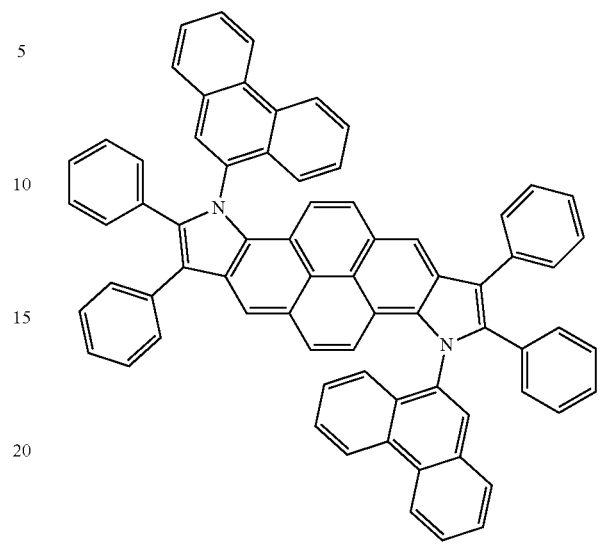
36
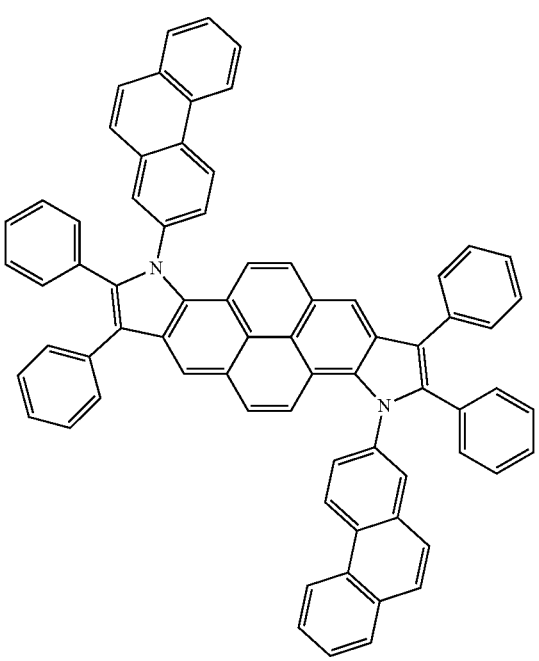

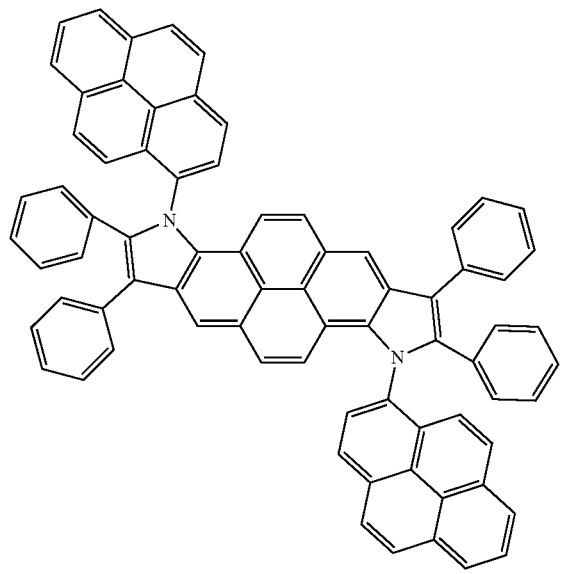
37
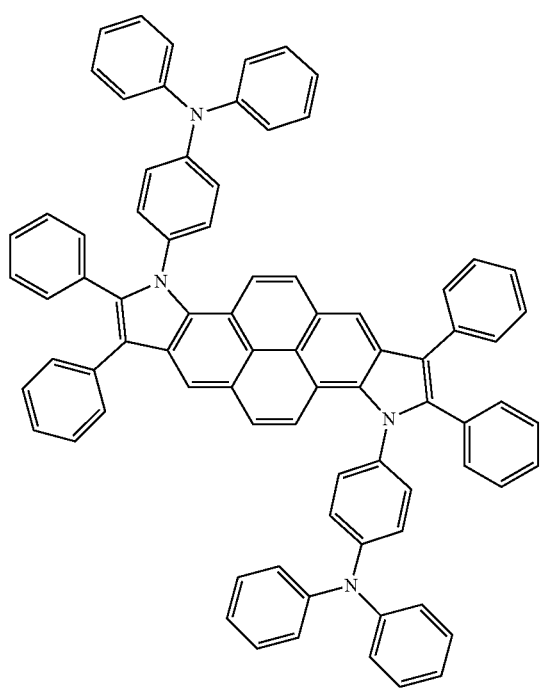
38
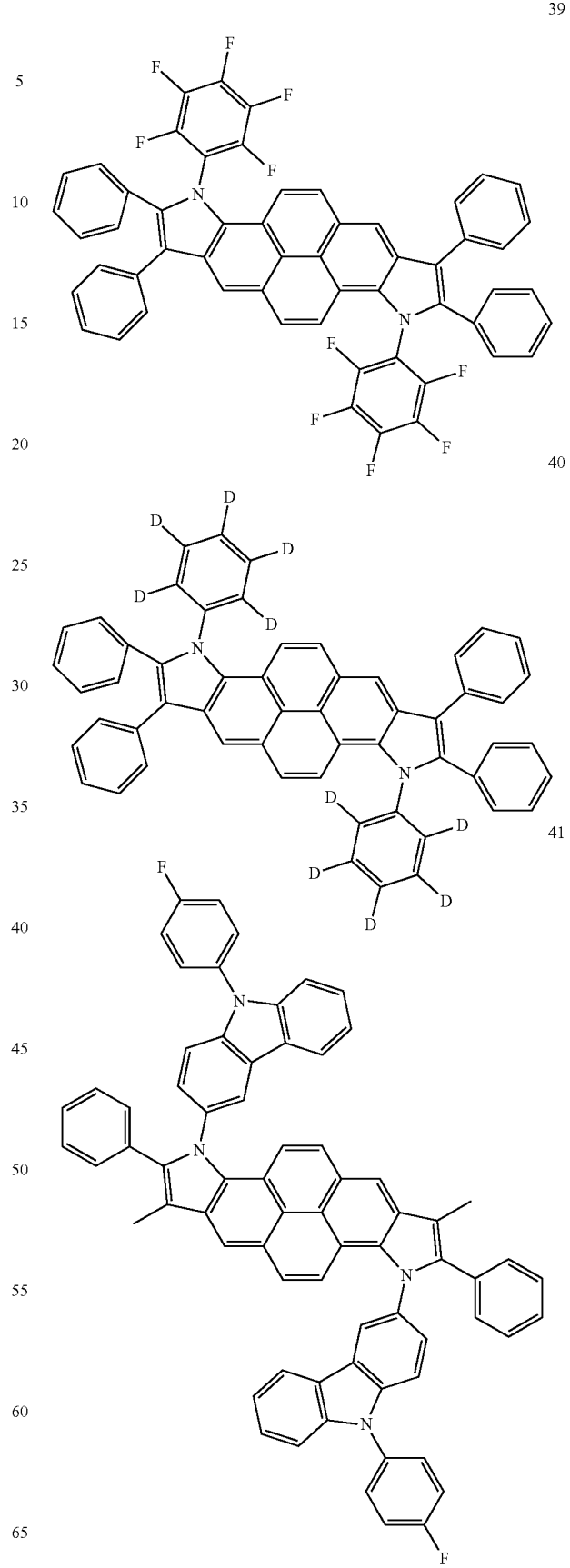

42
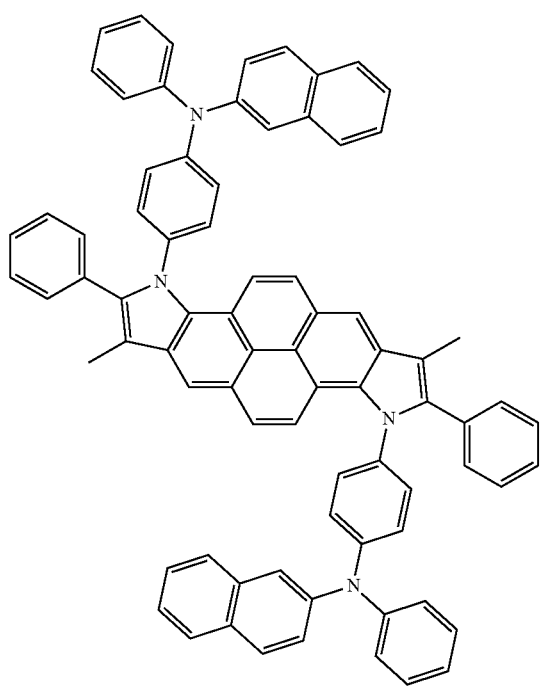
43
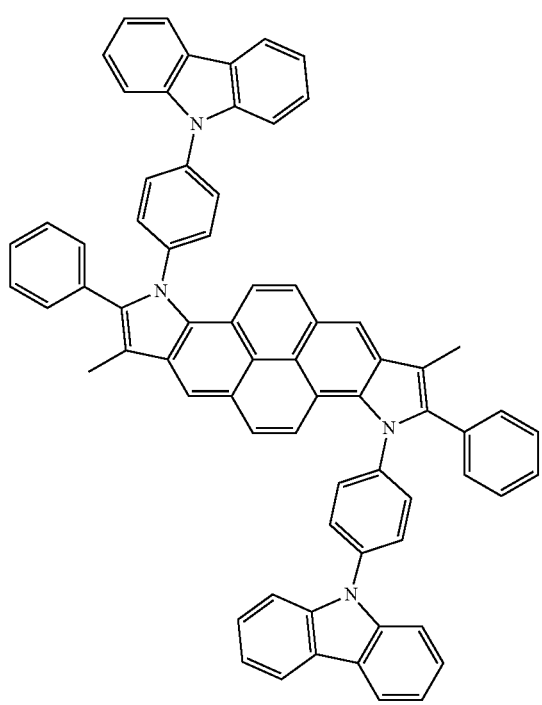
44
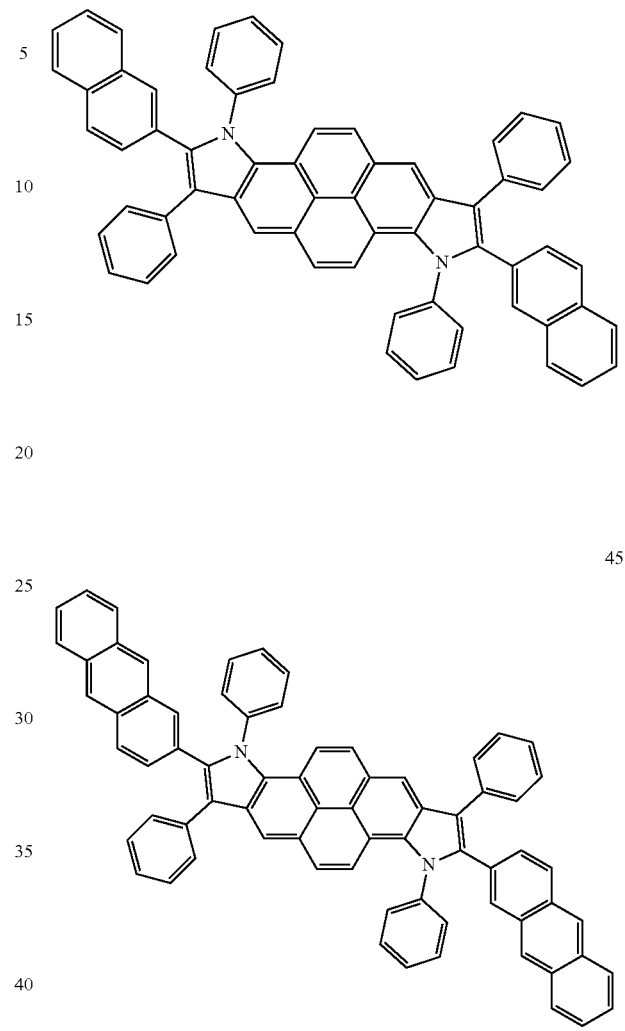
45
46
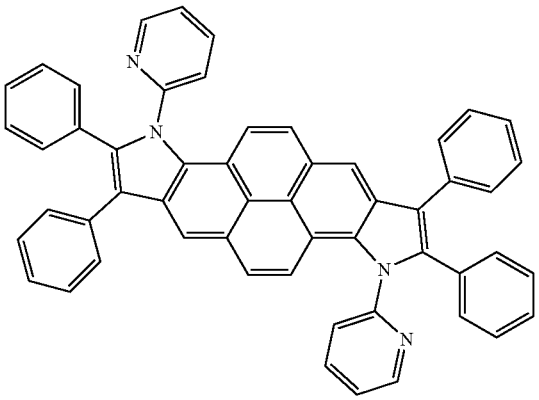

47
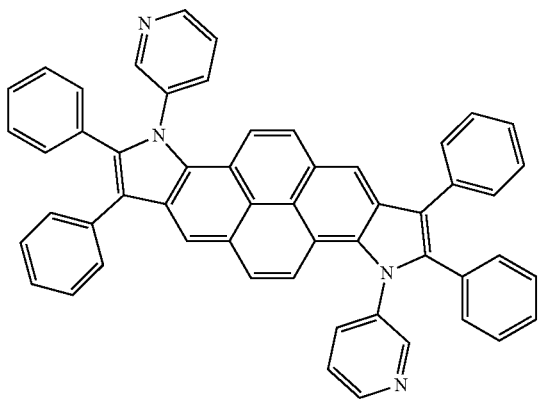
48
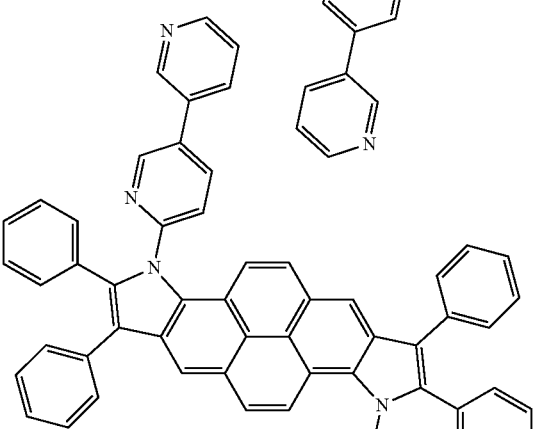
49
50
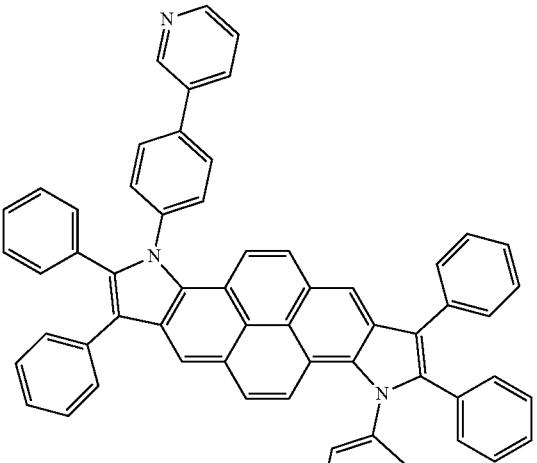
51
52
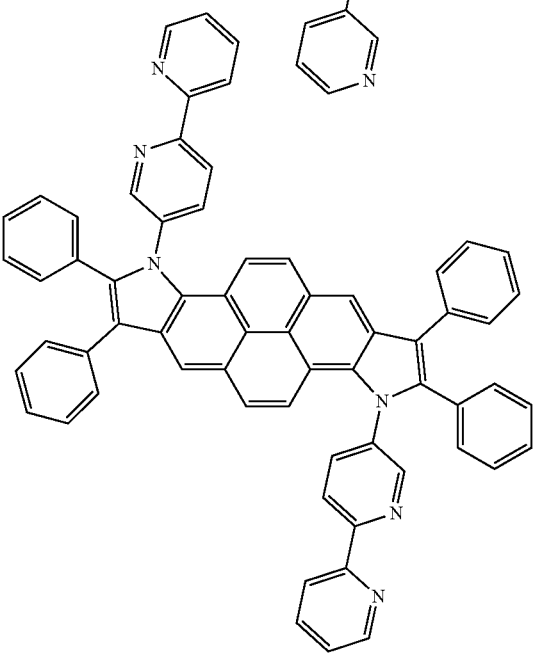

85
-continued
53
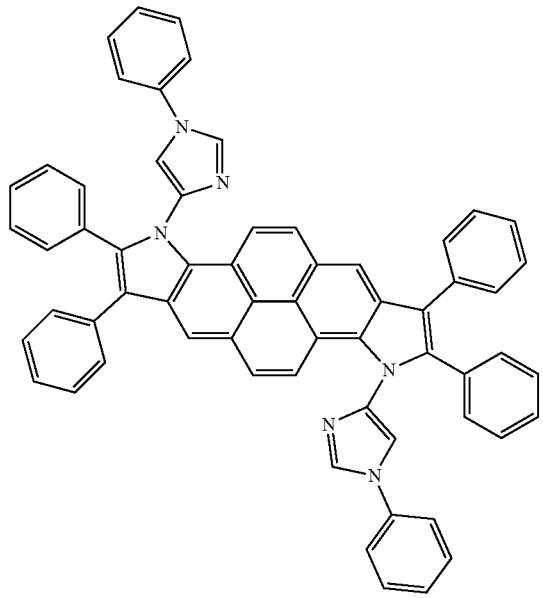
86
-continued
54
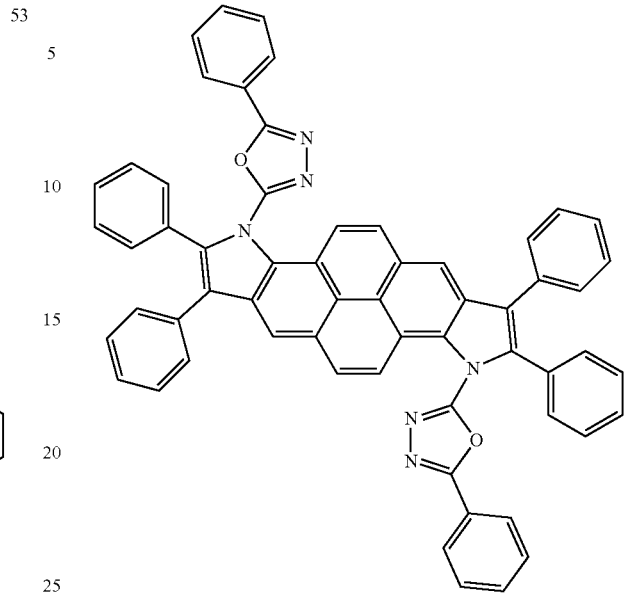
* * * * *